(12) United States Patent
Elliman

(10) Patent No.: US 11,026,994 B2
(45) Date of Patent: *Jun. 8, 2021

(54) SYNDECAN-2 COMPOSITIONS AND METHODS OF USE

(71) Applicant: ORBSEN THERAPEUTICS LIMITED, Galway (IE)

(72) Inventor: Stephen Joseph Elliman, Galway (IE)

(73) Assignee: ORBSEN THERAPEUTICS LIMITED, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/254,378

(22) Filed: Jan. 22, 2019

(65) Prior Publication Data
US 2019/0365851 A1 Dec. 5, 2019

Related U.S. Application Data

(63) Continuation of application No. 14/785,001, filed as application No. PCT/EP2014/057830 on Apr. 16, 2014, now Pat. No. 10,251,934.

(30) Foreign Application Priority Data

Apr. 16, 2013 (EP) ....................... 1306886
Aug. 14, 2013 (EP) ....................... 1314544

(51) Int. Cl.
| | | |
|---|---|---|
| A61K 38/17 | (2006.01) | |
| A61K 35/12 | (2015.01) | |
| C07K 14/71 | (2006.01) | |
| C07K 16/28 | (2006.01) | |
| A61K 39/00 | (2006.01) | |

(52) U.S. Cl.
CPC ............ *A61K 38/177* (2013.01); *A61K 35/12* (2013.01); *C07K 14/71* (2013.01); *C07K 16/28* (2013.01); *A61K 2035/122* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 5,486,359 | A | 1/1996 | Caplan et al. |
| 5,726,058 | A | 3/1998 | Jalkanen et al. |
| 6,355,239 | B1 | 3/2002 | Bruder et al. |
| 6,531,295 | B1 | 3/2003 | Saunders et al. |
| 10,124,038 | B2 | 11/2018 | Elliman |
| 10,251,934 | B2 * | 4/2019 | Elliman ............... C07K 14/71 |
| 2003/0225018 | A1 | 12/2003 | Ekker et al. |
| 2004/0258670 | A1 | 12/2004 | Laughlin et al. |
| 2005/0059147 | A1 | 3/2005 | Seshi |
| 2005/0226864 | A1 | 10/2005 | Hinton et al. |
| 2006/0078993 | A1 | 4/2006 | Phan et al. |
| 2007/0264239 | A1 | 11/2007 | Huard et al. |
| 2008/0241246 | A1 | 10/2008 | Sakthivel et al. |
| 2010/0247577 | A1 | 9/2010 | Foussat et al. |
| 2014/0356398 | A1 | 12/2014 | Riddell et al. |
| 2015/0030615 | A1 | 1/2015 | Derr et al. |
| 2016/0215265 | A1 | 7/2016 | Elliman |
| 2019/0015331 | A1 | 1/2019 | Elliman et al. |

FOREIGN PATENT DOCUMENTS

| | | |
|---|---|---|
| CN | 1678734 A | 10/2005 |
| EP | 1795588 A1 | 6/2007 |
| EP | 2545928 A1 | 1/2013 |
| JP | 2016516797 A | 6/2016 |
| JP | 2017532965 A | 11/2017 |
| KR | 20080075959 A | 8/2008 |
| KR | 20100106744 A | 10/2010 |
| KR | 20120013915 A | 2/2012 |
| KR | 101309910 B1 | 9/2013 |
| WO | WO-02087609 A1 | 11/2002 |
| WO | WO-03046141 A2 | 6/2003 |
| WO | WO-03062386 A2 | 7/2003 |
| WO | WO-2008100083 A1 | 8/2008 |
| WO | WO-2009012357 A2 | 1/2009 |
| WO | WO-2009105624 A2 | 8/2009 |
| WO | WO-2010065239 A1 | 6/2010 |
| WO | WO-2011153458 A2 | 12/2011 |
| WO | WO-2012111997 A2 | 8/2012 |

(Continued)

OTHER PUBLICATIONS

Alvarez-Viejo, Maria: CD271 as a marker to identify mesenchymal stem cells from diverse sources before culture. World Journal of Stem Cells, vol. 7, No. 2, Jan. 1, 2015, p. 470.
Carlotti, Francoise, et al., "Isolated human islets contain a distinct population of mesenchymal stem cells," Islets, p. 164-173 May/Jun. 2010.
Chinese Patent Application No. 201380019351.0 Third Office Action dated Jan. 12, 2017.
Christianson and Belting, Heparan sulfate proteoglycan as a cell-surface endocytosis receptor. Matrix Biology, 35:51-55, 2014.
Chung et al., "Human Embryonic Stem Cell Lines Generated without Embryo Destruction." Cell Stem Cell, vol. 2, No. 2, 2008, pp. 113-117.

(Continued)

*Primary Examiner* — Bridget E Bunner
*Assistant Examiner* — Fozia Hamud
(74) *Attorney, Agent, or Firm* — Wilson Sonsini Goodrich & Rosati

(57) ABSTRACT

SDC2, compositions that comprise SDC2, vectors encoding SDC2 and compounds that modulate expression of SDC2 by cells are used for treatment of mammalian, e.g. human, cells to achieve immunomodulation or for other specific therapeutic interventions. Cells are treated by combining the cells with SDC2, treating the cells with an antibody or fragment thereof that binds SDC2 or modulating expression or activity of SDC2 by the cells. Cells or tissue are derived from treated cells for therapeutic uses based on their immunomodulatory or other therapeutic properties.

20 Claims, 8 Drawing Sheets

Specification includes a Sequence Listing.

(56) References Cited

FOREIGN PATENT DOCUMENTS

| WO | WO-2013117761 A1 | 8/2013 |
|----|------------------|--------|
| WO | WO-2013172793 A1 | 11/2013 |
| WO | WO-2014168548 A2 | 10/2014 |
| WO | WO-2014170411 A1 | 10/2014 |
| WO | WO-2015038075 A1 | 3/2015 |
| WO | WO-2018220442 A2 | 12/2018 |

OTHER PUBLICATIONS

Chinese Patent Application No. 201480025184.5 Office Action dated Jul. 4, 2018.
Costabel et al., Pirfenidone in idiopathic pulmonary fibrosis: Expert panel discussion on the management of drug-related adverse events. Adv. Ther., 31:375-391, 2014.
Cuthbert et al., "Single-platform quality control assay to quantify multipotential stromal cells in bone marrow aspirates prior to bulk manufacture or direct therapeutic use." Cytotherapy, 2012, vol. 14, No. 4, pp. 431-440.
Dieudonne et al. High Wnt signaling represses the proapoptotic proteoglycan syndecan-2 in osteosarcoma cells. Cancer Res 70(13):5399-5408 (2010).
Duffy et al., Mesenchymal stem cell inhibition of T-helper 17 cell-differentiation is triggered by cell-cell contact and mediated by prostaglandin E2 via the EP4 receptor. European Journal of Immunol., 41:2840-2851, 2011.
European Patent Application No. 14718403.0 Communication dated Apr. 6, 2017.
European Patent Application No. 14718403.0 Communication dated Mar. 6, 2018.
European Patent Application No. 14718403.0 Examination Report dated Jan. 2, 2019.
European Patent Application No. 15158384.6 Communication dated Apr. 7, 2017.
European Patent Application No. 15158384.6 Extended European Search Report dated Jul. 8, 2015, 10 pages.
European Patent Application No. 18190005.1 European Search Report dated May 3, 2019.
GB1202319.8 Search Report dated Jun. 11, 2012, 3 pages.
Gronthos et al. "Molecular and cellular characterisation of highly purified stromal stem cells derived from human bone marrow." (2003) Journal of Cell Science, vol. 116:1827-1835.
Hohki et al., Blockade of interleukin-6 signaling suppresses experimental autoimmune uveoretinitis by the inhibition of inflammatory Th17 responses. Experimental Eye Research, 91:162-170, 2010.
Horwitz et al., Clarification of the nomenclature for MSC: The international society for cellular therapy position statement. Cytotherapy, 7:393-395, 2005.
Hsu et al. Neural stem cells, neural progenitors, and neurotrophic factors. Cell Transplant 16(2):133-150 (2007).
Huang et al., Prognostic significance of altered expression of SDC2 and CYR61 in esophageal squamous cell carcinoma. Oncology Reports, 21:1123-1129, 2009.
"Human/Mouse Integrin [alpha]11 Antibody." Jun. 30, 2015 (Jun. 30, 2015), 1 page, Retrieved from the Internet: URL:http://www.rndsystems.com/pdf/MAB4235.pdf.
Indian Patent Application No. 1777/KOLNP/2014 Office Action dated May 31, 2018.
International Patent Application No. PCT/IB2018/000687 International Search Report and Written Opinion dated Dec. 5, 2018.
International Patent Application No. PCT/IB2018/000939 International Search Report and Written Opinion dated Dec. 19, 2018.
Jones, E., et al., "Large-Scale Extraction and Characterization of CD271+ Multipotential Stromal Cells From Bone in Health and Osteoarthritis," Arthritis & Rhuematism, vol. 62, No. 7, Jul. 2010, pp. 1944-1954.
Kaltz N et al: Novel markers of mesenchymal stem cells defined by genome-wide gene expression analysis of stromal cells from different sources. Experimental Cell Research, Academic Press, US, vol. 316, No. 16, (Oct. 1, 2010), pp. 2609-2617.

Keifer et al.: "Inhibition of NF-êB Activity by Thalidomide through Suppression of IêB Kinase Activity", Journal of Biological Chemistry, American Society for Biochemistry and Molecular Biology, US, vol. 276, No. 25, Jun. 22, 2001, pp. 22382-22387.
Khan et al., CD4+ T Cell-derived Novel Peptide Thp5 Induces Interleukin-4 Production in CD4+ T Cells to Direct T Helper 2 Cell Differentiation. J Biol Chem, 287, 2830-2835, 2011.
Kozanoglu, Ilknur, et al., "Human bone marrow mesenchymal cells express NG2: possible increase in discriminative ability of flow cytometry during mesenchymal stromal cell identification." Cytotherapy (2009) vol. 11, No. 5, pp. 527-533.
KR1317507 Abstract from STN CAPlus database (1 pg) (2015).
Lambaerts et al., The signalling mechanisms of syndecan heparen sulphate proteoglycans Current Opinion Cell Biol., 21(5):662-669 (2009).
Lim et al., Cell surface heparan sulfate proteoglycans control adhesion and invasion of breast carcinoma cells Molecular Cancer, 14:15, 18 pages, 2015.
Lim et al., Syndecan-2 regulation of morphology in breast carcinoma cells is dependent on RhoGTPases. Biochimica et Biophysica Acta, 1840:2482-2490, 2014.
Llinas, L, et al., "Expression profiles of novel cell surface molecules on B-cell subsets and plasma cells as analyzed flow cytometry," Immunology Letters, vol. 134, No. 2, Jan. 30, 2011, pp. 113-121.
Lyons and Parish, Determination of lymphocyte division by flow cytometry. Journal of Immunological Methods, 171:131-137, 1994.
Manon-Jensen et al., Proteoglycans in health and disease: the multiple roles of syndecan shedding FEBS Journal, 277(19):3876-3889, 2010.
Matesanz-Isabel et al., New B-cell CD molecules. Immunology Letters, 2011, vol. 134, No. 2, pp. 104-112.
Mytilinalou et al., Research Communication: Syndecan-2 is a key regulator of transforming growth factor beta 2/Smad2-mediated adhesion in fibrosarcoma cells. IUBMB Life, 65(2):134-143 (2013).
Nierhoff et al. New cell surface markers for murine fetal hepatic stem cells identified through high density complementary DNA microarrays. Hepatology 46(2):535-547 (2007).
Nish et al., T cell-intrinsic role of IL-6 signaling in primary and memory responses. Elife, 3:e01949, 21 page (2014).
Paris et al., Opposing Roles of Syndecan-1 and Syndecan-2 in Polyethyleneimine-mediated Gene Delivery. J Biol Chem, 283:7697-7704, 2008.
Parish, Fluorescent dyes for lymphocyte migration and proliferation studies. Immunology and Cell Biology, 77:499-508, 1999.
Park et al., Syndecan-2 mediates adhesion and proliferation of colon carcinoma cells. The Journal of Biological Chemistry, 277(33):29730-29736, 2002.
PCT Patent Application No. PCT/EP2016/056065 International Search Report and Written Opinion dated May 20, 2016.
PCT Patent Application No. PCT/US2016/023178 International Search Report and Written Opinion dated Jun. 13, 2016.
PCT/EP2013/052692 International Preliminary Report on Patentability under Chapter II completed Mar. 13, 2014.
PCT/EP2013/052692 International Search Report completed Jun. 10, 2013.
PCT/EP2013/052692 Written Opinion Report completed Jun. 10, 2013.
PCT/US2017/000091 International Search Report and Written Opinion dated May 12, 2017.
Pennock, Natahan D. et al. T cell response: naive to memory and everything in between. Adv. Physiol. Educ. 37:273-283 (2013).
Rovira-Clave, Xavier et al. Syndecan-2 can promote clearance of T-cell receptor/CD3 from the cell surface. Immunology, 137(3):214-225 (Nov. 2012):E-Pub: Oct. 2, 2012.
Rozemuller, H., et al., Prospective isolation of mesenchymal stem cells from multiple mammalian species using cross-reacting anti-human monoclonal antibodies. Stem Cells and Development, vol. 19, No. 12, Dec. 1, 2010, pp. 1911-1921.
Ruiz et al., Syndecan-2 is a novel target of insulin-like growth factor binding protein-3 and is over-expressed in fibrosis. Plos One, 7(8):1-4, 2012.
Russian Patent Application No. 2014136711 Official Action dated Feb. 23, 2017.

(56) References Cited

OTHER PUBLICATIONS

Sanz-Nogués et al.: Angiogenic assessment of ORBCEL TM, a novel stromal cell population for treating Critical Limb Ischaemia (CLI); Cytotherapy, vol. 19, S198 (2017).
Sattler et al.: "Inhibition of T-Cell Proliferation by Murine Multipotent Mesenchymal Stromal Cells is Mediated by CD39 Expression and Adensoine Generation", Cell Transplantation, vol. 20, No. 8, Sep. 1, 2011, pp. 1221-1230.
Shi et al., Syndecan-2 exerts antifibrotic effects by promoting caveolin-1-mediated transforming growth factor-β receptor I internalization and inhibiting transforming growth factor-β1 signaling. Am J Respir Crit Care Med, 188:831-841, 2013.
Si et al. CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Silva et al. "The Profile of Gene Expression of Human Marrow Mesenchymal Stem Cells" (2003) Stem Cells: vol. 21: 661-669.
Stepp et al., Syndecan-1 and its expanding list of contacts. Advances in Wound Care, 4(4):235-249, 2015.
Tang et al., Calcitriol suppresses antiretinal autoimmunity through inhibitory effects on the Th17 effector response. The Journal of Immunology, 182:4624-4632, 2009.
Technical Data Sheet, Purified Mouse Anti-human CD271, Jun. 6, 2013, p. 1-2.
Teixe et al., Corrigendum to "Syndecan-2 and -4 expressed on activated primary human CD4+lymphocytes can regulate T cell activation." Molecular Immunology, 51:368, 2012.
Teixe et al., Syndecan-2 and -4 expressed on activated primary human CD4+ lymphocytes can regulate T cell activation. Molecular Immunology, 45:2905-2919, 2008.
Theocharis et al., Insights into the key roles of proteoglycans in breast cancer biology and translational medicine. Biochimica et Biophysica Acta, 1855:276-300, 2015.
U.S. Appl. No. 14/377,597 Final Office Action dated Jan. 14, 2019.
U.S. Appl. No. 14/377,597 Office Action dated Apr. 7, 2016.
U.S. Appl. No. 14/377,597 Office Action dated Aug. 15, 2018.
U.S. Appl. No. 14/377,597 Office Action dated Jan. 30, 2017.
U.S. Appl. No. 14/377,597 Office Action dated May 12, 2017.
U.S. Appl. No. 14/377,597 Office Action dated Nov. 6, 2015.
U.S. Appl. No. 14/377,597 Office Action dated Sep. 9, 2016.
U.S. Appl. No. 14/785,001 Final Office Action dated Jun. 27, 2018.
U.S. Appl. No. 14/785,001 Office Action dated Feb. 15, 2017.
U.S. Appl. No. 14/785,001 Office Action dated Jun. 20, 2016.
U.S. Appl. No. 15/074,681 First Action Interview Pilot Program Pre-Interview Communication dated Dec. 9, 2016.
U.S. Appl. No. 15/074,681 Office Action dated Apr. 27, 2017.
U.S. Appl. No. 15/074,681 Restriction Requirement dated Aug. 22, 2016.
U.S. Appl. No. 15/089,435 Final Office Action dated Sep. 3, 2019.
U.S. Appl. No. 15/089,435 Non-Final Office Action dated Nov. 14, 2018.
U.S. Appl. No. 15/089,435 Office Action dated Oct. 4, 2017.
U.S. Appl. No. 16/009,048 Restriction Requirement dated Jun. 28, 2019.
UNIPROT:P34741, XP002726498, 3 pages, printed Jun. 26, 2014, http://ibis.internal.epo.org/exam/dbfetch.jsp?id=UNIPROT* p. 3474I.
Wieczorek et al., Gene expression profile of mouse bone marrow stromal cells determined by cDNA microarray analysis.Cell Tissue Res. 311(2):227-237 (2003).
Yan, Xin-Long, et al., "Migration of Dorsal Aorta Mesenchymal Stem Cells Induced by Mouse Embryonic Circulation," Dynamics 240: 65-74 (2011).
Brazilian Patent Application No. 112015026258-9 Search Report dated Oct. 29, 2019.
Canadian Patent Application No. 2,909,356 Office Action dated Mar. 3, 2020.
Davey et al.: Mesenchymal stem cell-based treatment for microvascular and secondary complications of diabetes mellitus. Frontiers in Endocrinology 5:86 [1-16]. doi: 10.3389/fendo.2014.00086 (2014).
Final Report Summary—REDDSTAR (Repair of Diabetic Damage by Stromal Cell Administration). European Commission https://cordis.europa.eu/result/rcn/197094_en.html 1-28 (2017).
Final Report Summary—Core of Report—REDDSTAR (Repair of Diabetic Damage by Stromal Cell Administration). European Commission https://cordis.europa.eu/docs/results/305/305736/final1-reddstar-final-report-core-of-report.pdf 1-44 (2017).
Hagymasi et al.: Stem cell treatment in the treatment of gastrointestinal diseases. Orvosi Hetilap. 149(31):1449-1455 (2008).
Japanese Patent Application No. 2017-550240 Office Action dated Mar. 2, 2020.
Mendez-Ferrer et al.: Mesenchymal and haematopoietic stem cells form a unique bone marrow niche. Nature, 466:829-836 (2010).
Mendez-Ferrer et al.: Mesenchymal and haematopoietic stem cells form a unique bone marrow niche Nature, 466:829-836 (2010) Supplementary Information, 21 pages.
Patil et al.: Enhancement of wound healing with increased angiogenesis in a diabetic rabbit ulcer model by topical application of CD362+ human mesenchymal stem cells (Cyndacel-M) seeded in Excellagen scaffold. Tissue Engineering Part A, 21(Supp. 1):S90 XP05509717 (2015).
PCT/IB2018/000687 International Search Report and Written Opinion dated May 12, 2018.
U.S. Appl. No. 16/009,048 Office Action dated Dec. 13, 2019.

* cited by examiner

SYNDECAN-2 COMPOSITIONS AND METHODS OF USE

CROSS REFERENCE TO RELATED APPLICATIONS

This application is a continuation of U.S. application Ser. No. 14/785,001 filed Oct. 16, 2015, now issued as U.S. Pat. No. 10,251,934 on Apr. 9, 2019, which is a U.S. National Phase of International Application No. PCT/EP2014/057830 filed Apr. 16, 2014, which claims the benefit of UK Application Serial Number 1314544.6 filed on Aug. 14, 2013, and UK Application Serial Number 1306886.1 filed on Apr. 16, 2013, which are incorporated by reference in its entirety.

SEQUENCE LISTING

The instant application contains a Sequence Listing which has been submitted electronically in ASCII format and is hereby incorporated by reference in its entirety. Said ASCII copy, created on Aug. 15, 2019, is named 49707_704_301 SL and is 9,415 bytes in size. No new matter is introduced through incorporation of the Sequence Listing.

INTRODUCTION

The present invention relates to immuno-modulatory and therapeutic agents and compositions, and uses thereof. In addition the invention relates to testing and modifying existing cell-based products so as to affect their immuno-modulatory and/or other therapeutic properties.

BACKGROUND

A plurality of mesenchymal stem cell (MSC) related products, for clinical use, are known and more products are in development and are expected to be approved for human use in the future. MSCs exhibit some immuno-modulatory properties, which can contribute to their therapeutic value, and MSCs are used, inter alia, for treatment of autoimmune diseases. The immunosuppressive potential of human MSCs is evidenced for example by studies showing the inhibitory effects on the proliferation of T-cells, B-cells, dendritic cells and natural killer cells (Han et al., 2012).

EP 1795588 describes use of adipose tissue derived MSCs for treatment of graft versus host disease (GVHD); the cells are said to exert immunosuppressive properties.

EP 2545928 relates to MSC-containing cell preparations whose immunosuppressive ability is maintained by means of serum-free or low serum culture.

WO 2012/111997 discloses a combination therapy in which MSCs are given with immunoregulatory T cells, to achieve suitable immunosuppression for the MSC-based therapy.

WO 2009/1105624 discloses compositions and methods relating to the co-delivery of a molecule and a polypeptide to cells to improve the therapeutic efficacy of the molecules. Delivery of growth factors is improved by co-delivering these growth factors with their receptors and co-receptors; such as syndecans 1, 2, 3 and 4. Co-delivery of syndecans with growth factors protects the growth factors from proteolysis, enhances their activity, and targets the growth factors to the cell surface to facilitate growth factor signalling.

KR1020100106744 relates to a composition for preventing or treating migratory dermatitis or melanogenesis-associated diseases. The composition for preventing or treating migratory dermatitis contains syndecan-2 as an active ingredient. The migratory dermatitis conditions considered are melanoma, hyperpigmentation, hypopigmentation or vitiligo.

WO 02/087609 relates to a pharmaceutical composition for preventing papillomavirus infection in a mammal comprising, a soluble peptide, protein, or fusion protein that binds to papillomavirus particles as a ligand for syndecans having heparan sulfate glycosaminoglycan chains attached.

WO 03/062386 relates to methods and materials related to modulating syndecan levels and angiogenesis in an animal. Syndecan polypeptides and nucleic acids encoding syndecan polypeptides are disclosed. These are used to produce polynucleotides and polynucleotide analogues for modulating angiogenesis. Methods for identifying syndecan- and angiogenesis-modulating agents are also discussed.

Mukhopadhyay, A. et al., *J. Trauma Injury Infect. Crit. Care,* 2010, vol. 68, pp. 999-1008 concludes that syndecan-2 and FGF-2 may interact with each other, resulting in the shedding of syndecan-2 from cells and which in turn activates events responsible for a keloidic phenotype.

Kaur, C. et al., *Glia,* 2009, vol. 57, pp. 336-349, examines syndecan-2 expression in the amoeboid microglial cells and notes that this is up-regulated by hypoxia.

Contreras, H. R. et al., *Biochem. Biophys. Res. Comm.,* 2001, vol. 286, pp. 742-751, examines syndecan-2 expression in cancer, and notes that syndecan-2 expression is involved in differentiation of certain cells towards a migratory mesenchymal-like phenotype.

Sojoong Choi, et al., *Biochem. Biophys. Res. Comm.,* 2012, vol. 417, pp. 1260-1264, examined the role of matrix metalloproteinase-7 (MMP-7) on shedding of syndecan-2 from colon cancer cells. It was observed that MMP-7 directly mediates shedding of syndecan-2 from these cells.

Alexopoulou, A. N. et al., *BMC Cell Biol., vol.* 9, 2008, doi:10:10.1186/1471-2121-9-2 investigated vectors useful for the long term expression of transgenes during stem cell differentiation towards mesoderm. One of the vectors used encodes syndecan-2.

WO 2011/153458 discloses a method of interfering with dengue infection comprising interfering with dengue virus binding to a syndecan present on a cell targeted by dengue virus. Also disclosed are pharmaceutical compositions relating to this purpose.

Mytilinaiou, M. et al., *IUBMB Life,* 2013, vol. 65, pp. 134-143 examined the role of syndecan-2 as a regulator of cellular adhesion of fibrosarcoma cells that is mediated by TGFβ2/Smad2.

Kim, Y. et al., *Oncogene* (2003), vol. 22, pp. 826-830 observed that reduced syndecan-2 expression correlates with trichostatin-A-induced morphological changes and reduced tumorigenic activity in colon carcinoma cells. In addition downregulation of syndecan-2 expression by antisense cDNA mimicked the morphological changes and reduced anchorage-independent growth of colon cancer cells.

Chung, H. et al., *Journal of Biological Chemistry, vol.* 287, no. 23, pp. 19326-19335, 2012, found that melanocortin 1 receptor regulates melanoma cell migration by controlling syndecan-2 expression. This is because melanocortin 1 receptor inhibits activation of p38 MAPK, subsequently enhancing syndecan-2 expression and migration in melanoma cells.

Péterfia, B. et al., *PLoS ONE, vol.* 7, no. 6, e39474, observed that syndecan-1 enhances malignancy of a mesenchymal tumour cell line, via induction of syndecan-2 expression. Thus, syndecan-1 enhances proliferation, migration and metastasis of human fibrosarcoma cell-line cells in cooperation with syndecan-2.

Ruiz, X. et al., *PLoS ONE*, vol. 7, no. 8, e43049, describe their findings that syndecan-2 is a novel target of insulin-like growth factor binding protein-3 (IGFBP-3) and that syndecan-2 is over-expressed in fibrosis. The increased SDC2 expression is due, at least in part, to the activity of two pro-fibrotic factors, TGFβ and IGFBP-3.

Dieudonné, F-X et al., *Journal of Bone and Mineral Research*, vol. 27, no. 10, pp. 2118-2129, describe how syndecan-2 expression is upregulated by doxorubicin in osteosarcoma cells. T-cell factor (TCF) is responsible for inhibition of syndecan-2. Thus, targeted inhibition of TCF activity promotes syndecan-2 expression and sensitization to doxorubicin in osteosarcoma cells and bone tumours in mice.

KR 20120013915 describes a composition for diagnosing colon cancer containing an agent for measuring expression level of syndecan-2 peptide fragments. The agent contains an antibody which is specific to a syndecan-2 peptide fragment.

Huang, X. et al., *Oncology Reports* 2009, vol. 21, pp. 1123-1129, discusses the prognostic significance of altered expression of syndecan-2 (SDC2) and cysteine-rich 61 (CYR61) in oesophageal squamous cell carcinoma.

A common problem in the art is that there is insufficient immunosuppression for MSC-based products to be used on their own or that the immunosuppressive properties of the MSCs are lost, i.e. not maintained, over time in cell culture passage. It is desirable to retain, stimulate or to be able to recover these properties.

Immunosuppressive regimens can be used to prevent or reduce transplant rejection, and clinically used immunosuppressive regimens typically include a combination of several agents used concurrently. It is desirable to identify alternative immunosuppressive agents and therapies. Similarly, it is desirable to identify agents and therapies that promote angiopoiesis. Further, it is desirable to be able to assay the potency of potential therapeutic products in this field. A proposed assay is based upon soluble TNFR1 but alternative and preferably improved assays are needed.

OBJECTS OF THE INVENTION

An object of the present invention is to provide alternative agents and therapies that are immuno-modulatory and/or have other therapeutic properties as specified herein. An object of particular embodiments of the invention is to provide agents and therapies for use in rendering a product or composition comprising cells or tissue less immunogenic or more immunosuppressive.

SUMMARY OF THE INVENTION

In use of embodiments of the invention it has been shown that increased Syndecan-2 (SDC2) expression and/or activity enhances immunosuppression and/or has other therapeutic properties. Accordingly, the present invention provides SDC2, compositions comprising SDC2, vectors encoding SDC2 and compounds that modulate expression of SDC2 for use in treatment of cells—those cells then being for therapeutic use. These compositions, vectors and compounds per se can be used in therapeutic treatments, especially of humans, e.g. for immunomodulation or for other therapeutic uses as described herein.

The invention also provides methods of treating a population of cells comprising combining the cells with SDC2, treating the cells with an antibody or fragment thereof that binds SDC2 and/or modulating expression or activity of SDC2 by the cell or cells. The cells produced by the methods and also cells and tissue derived from treated cells form other parts of the invention.

Details of the Invention

Embodiments of the invention include compositions that comprise SDC2, methods that use SDC2 and specific uses of SDC2. Suitably this is in soluble form, and in particular embodiments it is human or horse SDC2, though SDC2s generally from mammals are included in the invention, in particular SDC2 from human, mouse, rat, dog, horse, rabbit, sheep, cow and pig.

The compositions can comprise a pharmaceutically acceptable excipient and/or carrier, being suitable for use in medicine. The compositions can include or be formulated as a cell culture medium—e.g. SDC2 in a cell culture medium—being suitable for use in cell culture, e.g. for addition to cells being cultured in preparation of a therapeutic cell-based product. The compositions can be formulated for sustained release and optionally modified to improve half-life, e.g. the SDC2 (or fragment, variant, derivative or analogue) can be PEGylated or PSAylated. The compositions may be formulated for injection, e.g. in water or saline solution for injection. The compositions may be formulated for inhalation, e.g. by nebulisation. The SDC2 can be made in recombinant form or isolated from cells that express or overexpress SDC2. In examples tested, SDC2 has been isolated from a supernatant of cells expressing SDC2 and has been made recombinantly; as noted elsewhere SDC2 may be shed into culture medium and hence can be harvested from cultures of SDC2 expressing cells.

The invention also provides an expression vector encoding SDC2; again preferably human or horse SDC2 though vectors encoding SDC2 generally from the mammals mentioned also form embodiments of the invention. The term "expression vector" denotes a nucleic acid, e.g. DNA or RNA, linear or circular, that comprises a segment encoding SDC2 operably linked to additional segments that provide for its transcription. Such additional segments may include promoter (many are known, suitable examples include CMV and UbC promoters), terminator and UTR sequences, and may optionally include one or more origins of replication, one or more selectable markers, an enhancer, a polyadenylation signal, and the like. Expression vectors are generally derived from plasmid or viral DNA, or may contain elements of both. One suitable vector of the invention, used in an example below, is an adenoviral vector. Other suitable viral vectors include retroviruses, lentiviruses and adeno-associated viruses. Preferred vectors for expression of human SDC2 comprise a coding sequence from SEQ ID NO: 1 or 2 (e.g. without the polyA tail), or an allelic variant thereof, or an alternative nucleotide sequence that encodes SEQ ID NO: 3 or 4.

SDC2 can be shed by cells into the culture medium and this ectodomain shedding is a highly regulated direct action of enzymes generally referred to as sheddases. Matrix metalloproteinases (MMPs) are known as the sheddases of syndecans. In particular MMP-7 has been demonstrated to be necessary for SDC2 shedding (Ryu et al., 2007). However a variety of extracellular stimuli including growth factors (Subramanion et al., 1997), chemokines (Li et al., 2002; Brule et al., 2006; Charnaux et al., 2005), heparanase (Yang et al., 2007), and cell stress (Fitzgerald et al., 2000) have also been demonstrated to induce shedding of SDC2.

In a specific embodiment of the invention, described in more detail below, SDC2 shed into culture medium from the surface of human MSCs had immunosuppressive properties when that SDC2-containing medium was used to treat a separate cell population. Hence, the invention provides uses of SDC2 to provide this therapeutic effect, immunosuppression. Cells for therapy, e.g. transplantation, can be treated in this way, e.g. by exposure to SDC2, to reduce their immunogenic properties. An immunosuppressive effect achieved according to the invention may also be used in parallel with other cell based therapies, e.g. to reduce or delay the risk or incidence of adverse immune reactions in a patient. Thus SDC2 and SDC2-containing compositions of the invention, and also the vectors and compounds of the invention, may be administered to a patient in combination with another therapeutic composition, e.g. a cell therapy product, which may be or comprise MSCs and/or stromal stem cells.

Further provided by the invention are compounds that modulate expression of SDC2 by cells for use in treatment of cells. In embodiments of the invention, the compounds increase expression of SDC2. Examples of such compounds include compounds that activate p53, compounds that activate the ERK, p38 or JNK SAPK kinase pathway, compounds that activate the hypoxia inducible factor (HIF)-mediated pathway, compounds that agonize the TGF, BMP, Lefty, Nodal and Activin pathways, compounds that agonize the NOTCH pathway, for example Jagged1, Jagged2, DLL1, DLL2, DLL3 and Dll4, compounds that agonize the Hedgehog signaling pathway, compounds that agonize the WNT pathway, compounds that activate the Androgen Receptor or Estrogen Receptor pathway and compounds that activate the NFκB pathway. Examples of compounds for use in enhancing SDC2 expression include, p53 modulating chemotherapeutics (e.g. nutlins, 5-FU, doxorubicin, cisplatin, gemcitabine, taxol), HDAC inhibitors, PPAR agonists, DMOG (a hypoxia mimetic), forskolin, colforsin (a water-soluble version of forskolin, a cAMP stimulator), WY4,643 (pirinixic acid, a Peroxisome Proliferator Activated Receptor-α (PPARα) agonist), troglitazone (a ligand to both PPARα and PPARγ), splitomicin, Sir2 (a class 3 HDAC inhibitor), trichostatin A (a class ½ HDAC inhibitor), sodium phenylbutyrate (a HDAC inhibitor), valproic acid (a HDAC inhibitor) and SAHA (another HDAC inhibitor). Enhancing expression of SDC2 in a cell therapy product can thus be used to render it immunosuppressive or increase its immunosuppressive properties.

A problem addressed in the present invention is that of providing alternative immunomodulatory and/or other therapeutic interventions. In uses of the invention, the compositions, vectors and compounds may be used for therapeutic treatments.

For example, in one series of embodiments of the invention, the compositions, vectors or compounds are for use in a therapeutic treatment that comprises immunomodulation. Increasing SDC2 amount and/or expression and/or activity promotes immunosuppression; hence, the invention provides therapeutic treatments that comprise immunosuppression.

Compositions of the invention, and also the vectors and compounds of the invention, may be used, alone or in combination therapies such as mentioned herein, to treat diseases of the lung, such as ARDS, COPD and IPF. In tests it is found that stromal cells injected intravenously tend to accumulate up in the lung, showing that delivery to the lung can be achieved. SDC2 can also be nebulised for lung delivery.

Compositions and treatments of the invention that enhance SDC expression and/or activity and also the corresponding vectors and compounds of the invention are suitable in general for any indication that requires or would benefit from immunosuppression; these indications include graft transplants, psoriasis, asthma and indications that have an autoimmune component, such as allergies, colitis, dermatitis and inflammatory disorders in general.

In embodiments, compositions and treatments of the invention and also the vectors and compounds of the invention may be used in combination with anti-inflammatory agents such as anti-TNF antibodies, examples of such antibodies include infliximab (Remicade), adalimumab (Humira), certolizumab pegol (Cimzia), and golimumab (Simponi), or with a circulating receptor fusion protein such as etanercept (Enbrel). The invention may be used in combination with anti-CD3 antibodies, examples of such antibodies including muromonab-CD3, otelixizumab, teplizumab and visilizumab. The combination can be used in an immunosuppressive therapy; it can be used for the treatment or prevention of transplant rejection and other inflammatory or autoimmune conditions e.g. Crohn's disease, ulcerative colitis and type 1 diabetes, and for inducing immune tolerance.

In a specific embodiment of the invention, described in more detail below, increased SDC2 on the surface of human MSCs rendered the cells more immunosuppressive compared with control MSCs. Hence, the invention provides increased cellular expression or activity or amount of SDC2 to provide this therapeutic effect. Cells for transplantation can be treated in this way to reduce their immunogenic properties. An immunosuppressive effect achieved according to the invention may also be used in parallel with other cell based therapies, e.g. to reduce or delay the risk or incidence of adverse immune reactions in a patient. The treated cells of the invention may be administered to a patient in combination with another therapeutic composition, e.g. a cell therapy product, which may be or comprise MSCs and/or stromal stem cells.

Cells of the invention may be administered prior to at the same time or after the other therapeutic product. Cells of the invention may be administered in advance to assist in tolerizing the immune system of a patient to subsequent administration of a cell therapy product, e.g. transplant.

Compositions of the invention, and also the vectors and compounds of the invention, and also compositions, uses, methods and treatments of the invention that enhance SDC expression and/or activity, may be used to treat cancer. Cancers in general may be treated using the invention, specifically including hepatocellular carcinoma, cervical cancer, pancreatic cancer, prostate cancer, breast cancer, colon cancer, fibrosarcoma, medullablastoma, and astrocytoma.

In embodiments of the invention the cancer to be treated is a solid tumour. Further, embodiments of the invention comprise targeting the treatment to the cancer stroma—advantageously focussing the therapy on the cancer stroma, believed essential to support cancer maintenance and growth.

In a specific embodiment of the invention, described in more detail below, SDC2 demonstrated an anti-cancer effect with respect to each of pancreatic cancer, prostate cancer, breast cancer and colon cancer.

Compositions of the invention, and also the vectors and compounds of the invention, and also compositions, uses, methods and treatments of the invention that enhance SDC expression and/or activity, may be used to treat inflammation and/or inflammatory disease. Hence, an anti-inflammatory effect may be achieved using the invention.

In a specific embodiment of the invention, described in more detail below, SDC2 demonstrated an anti-inflammatory effect in an assay.

Compositions of the invention, and also the vectors and compounds of the invention, and also compositions, uses, methods and treatments of the invention that enhance SDC expression and/or activity, may be used for wound healing or bone healing, or to promote wound healing or bone healing.

In a specific embodiment of the invention, described in more detail below, cells expressing SDC2 significantly enhanced wound healing in a model. By analogy with other data herein, this supports analogous activity of SDC2 in wound healing, including diabetic wound healing and bone fracture healing Compositions of the invention, and also the vectors and compounds of the invention, and also compositions, uses, methods and treatments of the invention that enhance SDC expression and/or activity, may be used to treat various equine conditions, including laminitis, tendon injuries and exercise induced pulmonary haemorrhage (EIPH)—also known as "bleeding" or a "bleeding attack".

Also provided by the present invention is a pharmaceutical composition for treating a disease or disorder in an animal, in particular a mammal and for example a human or horse. The pharmaceutical composition suitably comprises a compound, composition or vector of the invention in an amount effective to treat the disease or disorder in the animal. The active agent of the invention may thus be administered with an acceptable pharmaceutical carrier. For example, the active agent may be administered in a pharmaceutically acceptable liquid medium for injection. Examples of liquid medium are saline, phosphate buffered saline, optionally also containing additional materials such as dimethylsufoxide (DMSO) and human serum albumin. Method of administering therapeutic proteins and peptides are known in the art. A method of treatment of an animal, preferably a human, is provided, comprising administering to the animal an active agent of the invention.

Pharmaceutical compositions disclosed herein are useful for medical and veterinary applications and may be administered to an individual alone, or in combination with other supplementary active ingredients, agents, drugs or hormones. The compositions may optionally include a pharmaceutically-acceptable carrier including a pharmacologically acceptable vehicle, stabilizer, diluent, additive, auxiliary or excipient. Useful pharmaceutically acceptable carriers include, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003).

A pharmaceutical composition disclosed herein can optionally include other pharmaceutically acceptable components including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable.

Various routes of administration can be useful for administering a therapeutic compound disclosed herein. As such, topical, enteral or parenteral routes of administration may be suitable and such routes include both local and systemic delivery of a therapeutic compound or composition disclosed herein. Compositions are intended for inhaled, topical, intranasal, sublingual, injection, infusion, instillation, rectal and/or vaginal use may be prepared according to any method known to the art for the manufacture of pharmaceutical compositions.

Separately or in conjunction with the above, increasing SDC2 amount and/or expression and/or activity promotes angiogenesis; hence such embodiments of the invention provide therapeutic treatment that comprise or promote angiogenesis.

Methods of treating a population of cells are provided by the invention, comprising combining the cells with SDC2. This can be achieved by combining the cells with (i) cells that express SDC2, or (ii) a composition or a compound according to other embodiments of the invention. In vitro and ex vivo treatments are included.

In other embodiments, the invention may be adapted to reduce SDC2 amount and/or expression and/or activity, to provide therapeutic treatments that comprise immunoactivation and/or immunostimulation.

The cells to be treated may be stem cells, e.g. stromal stem cells or MSCs, and are suitably mammalian cells, preferably human, mouse, rat, dog, horse, rabbit, sheep, cow or pig and especially horse and human cells.

The invention additionally provides methods of treating a population of cells, comprising modulating expression or activity of SDC2 by a cell or cells in the population. Again, in vitro and ex vivo treatments are included. The modulating expression or activity of SDC2 may modulate the immunosuppressive properties of the cells. It may increase the expression of SDC2 so as to increase another immunosuppressive property of the cells. It may increase the expression of SDC2 so as to increase another therapeutic property of the cells.

To treat cells, the cells may be treated with a compound that promotes expression of SDC2; examples are given elsewhere herein. The cells may be transfected with a vector that encodes SDC2.

The cells may be treated so as to increase their exogenous SDC2 expression, for example by exposure to culture or environmental conditions that increase SDC2 expression. A number of strategies may be used to stimulate SDC2 expression, especially in stem cells, including stromal stem cells and MSCs. These include p53 activation by specific biological factors, compounds or stresses; compounds, biological factors and stresses that activate the ERK, p38 or JNK SAPK kinase pathway; biological factors, compounds or stresses that activate the hypoxia inducible factor (HIF)-mediated pathway; biological factors, compounds or stresses that agonize the TGF, BMP, Lefty, Nodal and Activin pathways; biological factors, compounds or stresses that agonize the NOTCH pathway including Jagged1, Jagged2, DLL1, DLL2, DLL3, Dll14; biological factors, compounds or stresses that agonize the Hedgehog signaling pathway; biological factors, compounds or stresses that agonize the WNT pathway; biological factors, compounds or stresses that activate the Androgen Receptor or Estrogen Receptor pathway; and biological factors, compounds or stresses that activate the NFκB pathway.

In embodiments of the invention, SDC2 expression has been increased by direct or indirect activation of p53, a tumour suppressor protein. Without wishing to be bound by theory this may be due to the presence of a "putative" p53-binding site in the promoter of the SDC2 gene (e.g. on the human gene). That activation may be achieved in a number of ways, some known to the skilled person, e.g. HDAC inhibition, growth arrest, starvation, toxin exposure and/or chemotherapeutics.

Serum starvation (SS) and growth arrest (confluence) both stimulated SDC2 expression. Both SS and growth arrest are known p53 stimuli.

HDAC inhibitors and sirtuins may be used to increase SDC2 expression. In use of the invention, splitomicin, valproic Acid and 2-pyrrolidinone-n-butyric acid (PBA) all increased SDC2 RNA levels at 24 hrs, with robust stimulation by splitomicin, a Class III HDAC inhibitor. The sirtuin family of HDACs, including SIRT1 and SIRT2, may be used to increase SDC2 expression. The sirtuins are NAD-dependant HDACs and are reported to deacetylate p53 protein— acetylation of p53 is reported to be important for its trans-activation/transcription activity. Thus sirtuins are key regulators of p53 activity. Examples of sirtuins include nicotinamide, sirtinol, EX-527 and tenovins. In other testing of the invention, the solvent DMSO also increased SDC2 RNA levels. DMSO is also reported to contain HDAC inhibitor (p53 activation) capacity.

Inducing or causing hypoxia in the cells can be used to increase SDC2 expression; in another series of tests, the hypoxia mimetic DMOG (Dimethyloxaloylglycine) produced a very robust increase in SDC2 RNA. DMOG is a hypoxia mimetic, and other hypoxia mimetics for use in the invention include cobalt chloride, EDHB and desferrioxamine. Hypoxia is reported to stimulate p53 (via ATR/CHK1 kinases).

Toxins can be used to increase SDC2 expression, e.g. the environmental toxin benzo[a]pyrene-7,8-diol-9,10-epoxide (BPDE). Other p53 activators for use in the invention include use of gamma-irradiation, MDM2 inhibitors (nutilins) and chemotherapeutics such as cisplatin and gemcitabine.

Embodiments of the invention hence include treatment of cells to activate p53 in order to increase SDC2 expression and/or shedding.

The cells to be treated are suitably mammalian cells, preferably human, mouse, rat, dog, horse, rabbit, sheep, cow or pig and especially horse and human cells. Prior to treatment, expression of SDC2 by the cells may be low or absent, so the treatment provides SDC2 levels previously unseen on those cells. The expression levels prior to treatment may alternatively have been initially high but reduced over time and the treatment is to restore previous SDC2 expression levels, e.g. to restore immunosuppressive and/or other therapeutic properties that have been lost over time from cells or tissue.

Modulating the expression or activity of SDC2 may decrease the amount and/or activity and/or expression of SDC2 so as to decrease an immunosuppressive property of the cells. It may decrease the amount and/or activity and/or expression of SDC2 so as to decrease an angiopoietic property of the cells. Further embodiments of the invention provide methods comprising treating cells so as to induce immunostimulation and/or immunoactivation. Cells can be treated to ablate the native SDC2 expression; for example an antisense therapy or other therapy may be used to knock-out or knock-down SDC expression.

All methods of the invention further comprise deriving progeny cells or tissue from the treated cells; and the invention extends also to the cells or tissue obtained from those methods.

Levels of SDC2, both on cells and in cell medium, are thus linked, in embodiments of the invention, with immunomodulatory and/or other therapeutic properties. Still further provided by the present invention is a method of testing a cell therapy product, which may comprise cells and/or tissue, comprising testing for SDC2. This can be achieved using an assay based on binding to an antibody to SDC2, preferably a SDC2-specific antibody. Existing SDC2 ELISA methods are suitable. SDC2 can be measured on the cell surface or in the medium or both. SDC2 levels may be compared with a predetermined standard, elevated levels indicating presence of immunosuppressive and/or other therapeutic properties and reduced levels indicating absence thereof.

In an embodiment of the invention there is provided an assay for potency of a therapeutic product comprising cells, comprising assaying the cells for expression of SDC2 or assaying the product (e.g. the solution) for presence of SDC2. Another embodiment of the invention lies in use of SCD2 levels in an assay for potency of a cell therapy product.

Generally in use of the testing/assay methods of the invention, an ELISA can be employed to monitor SDC2 shedding and therefore efficacy of a particular batch of human MSCs.

Cells or products that fail the test/assay may be discarded or treated to increase their SDC2 expression. Assay of SDC2 can be used prior to deciding whether to treat cells or tissue according to other methods of the invention.

An assay protocol of the invention comprises:
1. assay SDC2 levels in the potential product;
2. compare this level with a predetermined minimum for an acceptable therapeutic product;
   a. if the level is at or above the minimum, the potential product is accepted;
   b. if the level is below the minimum, the product is not accepted;
3. optionally, next compare the level with a predetermined maximum for an unacceptable therapeutic product;
   a. if the level is below the maximum then the product is rejected;
   b. if the level is intermediate between the minimum for an acceptable therapeutic product and the maximum for an unacceptable therapeutic product then the potential product can be treated to try to increase its SDC2 level, and the assay then repeated.

The cut off SDC2 levels for the assay, the predetermined minimum and maximum levels mentioned, may vary according to other testing, the cells used, the nature of the therapy and other factors. The predetermined minimum level for a therapeutic product may be a SDC2 level of around 1200 pg/ml, 1300 pg/ml, 1400 pg/ml, 1500 pg/ml or a higher value. The predetermined maximum level for an unacceptable preparation may be around 200 pg/ml, 300 pg/ml, 400 pg/ml, 500 pg/ml or 600 pg/ml; it may be higher or lower than these stated values, though will generally be significantly lower than the minimum for an acceptable product. Alternatively, any preparations below the predetermined minimum for an acceptable therapeutic product may be regarded as unacceptable but suitable for treatment to try to raise the SDC2 level to an acceptable level.

In a specific example of the invention, described in more detail below, a poor MSC donor cell preparation failed the SDC2 assay whereas acceptable donors did not.

Hence, the invention provides a "batch release" or quality control potency assay for stem cell and other cell therapy patches or products to be checked before use, dispatch, etc.

Syndecan-2 (SDC2), also called Fibroglycan and now CD362, is a transmembrane (type I) heparan sulfate proteoglycan and is a member of the syndecan proteoglycan family. References herein to SDC2 refer generally to SDC2 of all species, including orthologues thereof, preferably human, mouse, rat, dog, horse, rabbit, sheep, cow and pig, especially horse and more preferably human.

The invention relates further to antibodies to SDC2, methods of treatment that use an antibody to SDC2, uses of an antibody to SDC2 and pharmaceutical compositions comprising an antibody to SDC2. An anti-Syndecan 2 antibody, orb13481, reactive with at least human, mouse and rat is available from Biorbyt Ltd. (12 Pembroke Avenue, Denny Industrial Centre, Waterbeach, Cambridge, CB25 9QR, UK). A further SDC2 antibody, catalog number: MAB29651 (Clone 305507) is available from R&D Systems, Inc, reactive with human, mouse, rat, equine, rabbit and pig. Antibodies to SDC2 fragments as disclosed herein are also embraced within the term anti-SDC2 antibody.

Data from examples of the use of SDC2 demonstrate the role of SDC2 as a dominant negative inhibitor of the activity of native SDC2. Hence, the invention provides therapeutic uses of a SDC2 antagonist, such as SDC2 or an antibody to SDC2, that correspond to the uses of SDC2 disclosed herein and of SDC2 positive cells disclosed in WO 2013/117761. The invention accordingly provides an antagonist to SDC2 (e.g. an antibody) for use in immunosuppression, treatment of inflammation, treatment of cancer and for wound/bone healing.

The invention accordingly further provides an antibody to SDC2 for use as a tumor suppressor. An antibody to SDC2 may be used for treatment of lung diseases including acute lung injury (ALI); acute respiratory distress syndrome (ARDS); chronic obstructive pulmonary disosorder (COPD); and idiopathic pulmonary fibrosis (IPF). An antibody to SDC2 may be used to treat sepsis and sepsis-induced multiorgan failure, bone marrow transplant (BMT) or haematopoietic stem cell (HSC) rejection; solid organ transplant (SOT) rejection (including liver, kidney, skin, cornea, heart, lung); acute toxin-induced liver failure; autoimmune hepatitis; primary biliary cirrhosis (PBC) and primary sclerosing cholangitis (PSC); osteonecrosis; degenerative disc disease; rheumatoid arthritis; osteoarthritis and delayed bone healing in diabetic patients; autoimmune nephritis including Wegener's granulomatosis (WG); burns, severe burns; muscle wasting conditions and atrophic syndromes including sarcopenia; cachexia and other muscle wasting conditions including the muscular dystrophies (Duchenne and Becker); congestive heart failure, acute myocardial infarction and stroke; type 1 diabetes; type 2 diabetes; diabetic retinopathy and other retinopathies; diabetic nephropathy and other nephropathies; diabetic neuropathy and other neuropathies; non-healing diabetic ulcers; diabetic cardiomyopathy and other myopathies; athersclerosis; peripheral artery disease and critical limb ischemia; uveitis; (wet or dry) acute macular degeneration (AMD); retinal and corneal damage; autoimmune conditions such as autoimmune gastritis (AIG); graft-versus-host disease (GvHD); multiple sclerosis and demyelinating diseases; thyroid disease; inflammatory bowel diseases including Crohn's disease, ulcerative colitiis and fistulising crohns disease; scleroderma; lupus (SLE); Graves' disease; and autoimmune lymphoproliferative disease (ALPS).

An antibody to SDC2 may also be used to treat various equine conditions, including laminitis, tendon injuries and exercise induced pulmonary haemorrhage (EIPH)—also known as "bleeding" or a "bleeding attack".

Antibodies useful in the invention include antibodies comprising the properties of binding to SDC2 and also binding to a second target. These antibodies may thus comprise a second binding domain that binds to another antigen, e.g. a cell surface antigen, and include bispecific antibodies as known generally in the art.

The term "antibody" comprises derivatives or functional fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also comprises immunoglobulins (Ig(s)) of different classes (i.e. IgA, IgG, IgM, IgD and IgE) and subclasses (such as IgG1, IgG2 etc.).

The term "antibody" also includes embodiments such as chimeric, single chain and humanized antibodies, as well as antibody fragments, like, inter alia, Fab fragments. Antibody fragments or derivatives further comprise F(ab')2, Fv, scFv fragments or single domain antibodies, single variable domain antibodies or immunoglobulin single variable domain comprising merely one variable domain, which might be VH or VL, that specifically bind an antigen or epitope independently of other V regions or domains. Such immunoglobulin single variable domains encompass not only an isolated antibody single variable domain polypeptide, but also larger polypeptides that comprise one or more monomers of an antibody single variable domain polypeptide sequence.

Reference to human SDC2 may further embrace polypeptides consisting of or comprising:
(a) an amino acid sequence as set out in SEQ ID NO: 3 or 4;
(b) naturally occurring variants of (a);
(c) orthologues of (a) or (b),
(d) biologically active and diagnostically or therapeutically useful fragments, analogues, variants and derivatives thereof,
(e) extracellular domains of (a)-(d), and
(f) dimers and oligomers of all the above.

The SDC2 polypeptides of the present invention may be recombinant polypeptide, natural polypeptide or synthetic polypeptide, preferably natural or recombinant polypeptide. The terms "fragment", "derivative", "variant" and "analogue" refer to a polypeptide which retains essentially the same biological function or activity as SDC2, and may be (i) one in which one or more of the amino acid residues are substituted with a conserved or non-conserved amino acid residue (preferably a conserved amino acid residue), or (ii) one in which one or more of the amino acid residues includes a substituent group, or (iii) one in which the mature polypeptide is fused with another compound, such as but not limited to a compound to increase the half-life of the polypeptide (for example, polyethylene glycol or polysialic acid), or (iv) one in which additional amino acids are fused to the mature polypeptide, for example but not limited to for facilitation of purification of the mature polypeptide.

The polypeptides of the present invention additionally include the polypeptides of SEQ ID NO: 3 and 4 (in particular the mature polypeptide) as well as polypeptides which have at least 60% similarity (preferably at least 60% identity) to the polypeptide of SEQ ID NO: 3 or 4, preferably at least 80% similarity (more preferably at least 80% identity) and more preferably at least 90% similarity (more preferably at least 90% identity) to the polypeptide of SEQ ID NO: 3 or 4 and still more preferably at least 95% similarity (still more preferably at least 95% identity) to the polypeptide of SEQ ID NO: 3 or 4 and also include portions of such polypeptides with such portions of the polypeptide generally containing at least 100 amino acids, preferably containing at least 120 and more preferably at least 140 amino acids. "Similarity" between two polypeptides is determined by comparing the amino acid sequence and its conserved amino acid substitutes of one polypeptide to the sequence of a second polypeptide. Various different approaches are known for the calculation of sequence similarity and identity. Generally, a suitable way to perform these calculations is to run database searches using a program such as Smith-Waterman, BLAST or FASTA, and use one or preferably two or even three similarity tables. The Blosum and PAM (Point Accepted Mutation) matrices are suitable amino acids similarity matrices for database searching and sequence alignment. If Smith-Waterman or FASTA is used then it is relevant to ensure the open gap penalty is large enough, and if the initial runs do not uncover any homologous sequences it can be appropriate to try a different algorithm—this is particularly true if you started with one of the heuristic algorithms, BLAST or FASTA.

In specific embodiments of the invention described in more detail in an example below, fragments of SDC2 have been made and tested for activity with respect to native, i.e. intact human SDC2. Active fragments were identified. Accordingly the invention also provides fragments of SDC2 that retain SDC2 activity—which indicates as elsewhere herein that the fragment will illustrate the characteristic activity of human SDC2 (though not necessarily with identical potency) in the assay of Example 2 or in the assay of Example 9 (i.e. producing a dose-dependent suppression of NFκB activation by TNFα or IL1β). Active fragments retain SDC2 activity and may exceed the activity of native SDC2; the fragments preferably retain at least 30%, at least 50%, at least 70% or at least 80% of the activity of native SDC2.

The invention hence includes and provides polypeptide comprising or consisting of a fragment of SDC2, wherein the polypeptide has SDC2 activity. The fragment suitably comprises up to 150, up to 120, up to 100 or up to 80 amino acids of SEQ ID NO: 3. Further, fragments of the invention separately may include the signal sequence of SDC2, namely amino acids 1-18 of SEQ ID NO: 3. The fragments are suitably at least 30, at least 40, at least 50 or at least 60 amino acids in length. Uses of the fragments, compositions comprising the fragments and methods of treatment using the fragments are as for the intact SDC2. The fragments constitute embodiments of SDC2.

Preferably, the term SDC2 refers to native ("intact") SDC2, to active fragments of SDC2, to active variants of SDC2 and to SDC2-type surface proteins that are recognized by antibodies to SDC2, preferably by SDC2-specific antibodies; preferably references to SDC2 refer to native SDC2 and active fragments thereof, more preferably to native SDC2. An SDC2 antibody is found as catalog number: MAB29651 (Clone 305507), available from R&D Systems, Inc, reactive with human, mouse, rat, equine, rabbit and pig. Human SDC2 according to the present invention tests positive in an assay for immunosuppression as per Examples 2 or 9 herein and more preferably binds to the SDC2 antibody.

Still further provided by the invention is an antibody to the polypeptide comprising or consisting of the fragment of SDC2. Such antibodies are suitable for use in human therapy, especially for use in (i) immunosuppression, (ii) treatment of inflammation, (iii) treatment of cancer, (iv) wound healing or (v) bone healing. Such antibodies are also suitable in therapies as described herein for antibodies to intact SDC2.

```
                                 Sequences

SEQ ID NO: 1-SDC2 human mRNA
      1   gcccggagaa   gcaggctcag   gagggaggga   gccagaggaa   aagaagagga   ggagaaggag 61   gaggacccgg   ggagggaggc   gcggcgcggg   aggaggaggg   gcgcagccgc   ggagccagtg 121   gccccgcttg   gacgcgctgc   tctccagata   ccccggagc    tccagccgcg   cggatcgcgc 181   gctcccgccg   ctctgccoct   aaacttctgc   cgtagctocc   tttcaagcca   gcgaatttat 241   tccttaaaac   cagaaactga   acctcggcac   gggaaaggag   tccgcggagg   agcaaaacca 301   caggagagca   agaagagctt   cagagagcag   ccttcccgga   gcaccaactc   cgtgtcggga 361   gtgcagaaac   caacaagtga   gagggcgccq   cgttccoggg   gcgcagctgc   gggcggcggg 421   agcaggcgca   ggaggaggaa   gcgagcgccc   ccgagcccg    agcccgagtc   cccgagcctg 481   agccgcaatc   gctgcggtac   tctgctccgg   atLcgtgtgc   gcgggctgcg   ccgagcgctg 541   ggcaggaggc   ttcgttttgc   cctggttgca   agcagcggct   gggagcagcc   ggtccctggg 601   gaatatgcgq   cgcgcgtqqa   tcctqctcac   cttgggcttg   gtggcctgcg   tgtcggcgga 661   gtcgagagca   gagctgacat   ctgataaaga   catgtaccTt   gacaacagct   ccattgaaga 721   agcttcagga   gtgtatccta   ttgatgacga   tgactacgct   tctgcgtctg   gctcgggagc
```

| | Sequences |
|---|---|
| 781 | tgatgaggat gtagagagtc cagagctgac aacatctcga ccacttccaa agatactgtt |
| 841 | gactagtgct gctccaaaag tqqaaaccac gacgctgaat atacagaaca agatacctgc |
| 901 | tcagacaaag tcacctgaag aaactgataa agagaaagtt cacctctctg actcagaaag |
| 961 | gaaaatggac ccagccgaag aggatacaaa tgtgLatact gagaaacact cagacagtct |
| 1021 | gtttaaacgg acagaagtcc tagcagctgt cattgctggt ggagttattg ctttctctt |
| 1081 | tgcaattttt cttatcctgc tgttggtgta tcgcatgaga aagaaggatg aaggaagcta |
| 1141 | tgaccttgga gaacgcaaac catccagtgc tgcttatcag aaggcaccta ctaaggagtt |
| 1201 | ttatgcgtaa aactccaact tagtgtctct atttatgaga tcactgaact tttcaaaata |
| 1261 | aagcttttgc atagaataat gaagatcttt gttttttgtt ttcattaaag agccattctg |
| 1321 | gcactttaat gataaaatcc cattgtattt aaaacatttc atgtatttct ttagaacaac |
| 1381 | ataaaattaa aatttaacat ctgcagtgtt ctgtgaatag cagtggcaaa atattatgtt |
| 1441 | atgaaaaccc tcgatgttca tggaattggt ttaaacttt atgcgcaaat acaaaatgat |
| 1501 | tgtcttttc ctatgactca agatgaaag ctgtttcatt tgtgtcagca tgtctcagat |
| 1561 | tgaccttacc aagttggtct tactttgtta atttatctgt tgtoccctc ctctcctctg |
| 1621 | ccctcccttc ttgtgccctt aaaaccaaac cctatgcctt ttgtagctgt catggtgcaa |
| 1681 | tttgtctttg gaaaattcag ataatggtaa tttagtgtat atgtgatttt caaaLaLgta |
| 1741 | aacULaact tccactttgt ataaattttt aagtgtcaga ctatccattt tacacttgct |
| 1801 | ttatttca ttacctgtag ctttgggcag atttgcaaca gcaaattaat gtgtaaaatt |
| 1861 | ggattattac tacaaaaccg tttagtcata tctatctaat cagatcttct tttgggagga |
| 1921 | tttgatgtaa gttactgaca agcctcagca aacccaaaga tgttaacagt attttaagaa |
| 1981 | gttgctgcag attcctttgg ccactgtatt tgttaatttc ttgcaatttg aaggtacgag |
| 2041 | tagaggttta aagaaaaatc agtttttgtt cttaaaaatg catttaagtt gtaaacgtct |
| 2101 | ttttaagcct ttgaagtgcc tctgattcta tgtaacttgt tgcagactgg tgttaatgag |
| 2161 | tatatgtaac agtttaaaaa aaaagttggt atttttataag cacagacaat tctaatggta |
| 2221 | acttttgtag tcttatgaat agacataaat tgtaaLttgg gaacataaaa actactgaat |
| 2281 | aaatcatgtg gcctaatatt gaaaatgtca ctgttataaa ttttgtacat ttttgatcaa |
| 2341 | atgtacatct cccctttgct aacggccgtc tgctctcaag gatgacgtgg gtttgatttc |
| 2401 | taagtgtttc acagtgtctg taaatcaaga ccaaagagcc tgtcgatgag actgtttatt |
| 2461 | accagattca cttctgaatt ggccagagga aatctgaatg tattatcctg LgtgLgtcta |
| 2521 | ggtagagata ttggaaggct gccaggggat ttcgaagttt gcaaccttta taggataact |
| 2581 | gatggcaata ttaagacaga cgcctgcttt tgcaaataac ttacaagact gtaaattcca |
| 2641 | aagatctgaa tggggctttc ctgatgttgg tatctaaggc ttaggcctat agattgattt |
| 2701 | accttggaa ttgtgctcca aatgtctact gaagcttaac cgaagaacta ataaatggac |
| 2761 | tacagtagct cacgttacag ggaaggaggg taggcaggga ggctctgtgt gttaaaatga |
| 2821 | gggtctcact gctttaggat tgaagtggct ggaaagagtg atgcctgggg aaggagatgg |
| 2881 | agttatgagg gtactgtggc tggtactttc tgtactaaac atttccttt tctattttac |
| 2941 | cactaatttt gttttaaact gtgagccgtc caagtcagaa gaagacagca aaaaaagcaa |
| 3001 | cttttccaac atacaattta ctttaataa agtatgaata tttcaLtttg agaacattcc |
| 3061 | ctggaattgc cacataattc attaaaaaca ttttttaag caacacttgg aacagtgttt |

-continued

```
                                    Sequences 3121    actttaaatc cttaatggcc ttaattaatt ctcagattcc tgocccatca cttacagaac 3181    caattcactt tagagtgact aaaaggaaac gatagcctag ctttctaaag ccacgctgtg 3241    tccctcaatt acagagggta ggaatgggta tacctctaac tgtgcaaagc agagtgaaat 3301    tcaattcata gaataacaac tgctgggaat atccgtgcca ggaaaagaaa aatttctggc 3361    aaatattttg tcactgctgt aaagcaaaat atttgtgaaa gtgccaaaat aaagtctgtc 3421    atgccaaaag taaaaaaaaa aaaaaaaaaa aaaaaaaaaa aaaaaaaaaa aaaaaaaaaa 3481    aaaaaaaaaa a SEQ ID NO: 2-nucleotides 605-1210 of SEQ ID NO: 1
(encoding SEQ ID NO: 3)

SEQ ID NO: 3-SDC2 human protein
  1     mrrawilitl glvacvsaes raeltsdkdm yldnssieea sgvypidddd yasasgsgad 61     edvespeltt srplpkillt saapkvettt lniqnkipaq tkspeetdke kvhlsdserk 121     mdpaeedtnv ytekhsdslf krtevlaavi aggvigflfa iflilllvyr mrkkdegsyd 181     lgerkpssaa yqkaptkefy a SEQ ID NO: 4-amino acids 19-201 of SEQ ID NO: 3
(the mature protein)
```

The invention is now described in the following examples, illustrated by the accompanying drawings in which:—

EXAMPLE 1—IMMUNOSUPPRESSION BY ENHANCED SDC2 EXPRESSION

Figure 1:
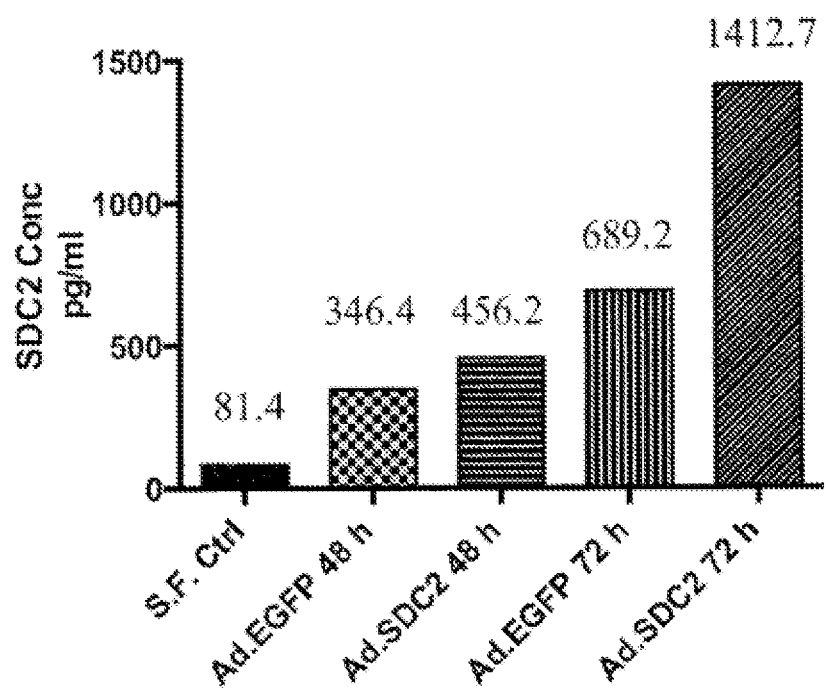
FIG. 1 shows detection of shed SDC2 in the supernatant of Ad.SDC2 expressing MSCs using ELISA.

Methods
Transduction of MSCs

MSCs were plated at a density of $10^5$ cells per well of a 6-well plate (Nunc) in complete media (α-MEM, 10% FBS) and left to adhere overnight. Cells were left untransduced as a negative control or transduced with 1 μl adenovirus (AD5 family) encoding human SDC2 (at $10^{12}$ vp/ml) and plates were spun at 800×g for 90 min at 37° C. The virus was left on the cells for approx. 4 hours and then washed off and replaced with serum-free media (1 ml/well).

Western Blot Analysis

Cells were harvested by trypsinisation and lysed in cell lysis buffer containing 50 mM Tris pH 7.4, 10% glycerol, 0.5% NP40, 150 mM NaCl and complete Mini Protease inhibitors (Roche). Cell lysates were subjected to 10% SDS-PAGE; 50 μg protein was loaded per track. Protein detection was performed by diluting anti-human Syndecan-2 Ab (R&D systems) 1:500 in TBS 0.1% Tween, 3% BSA. The secondary anti-Rat IgG antibody conjugated to horse-radish-peroxidase (Santa Cruz) was added at a dilution of 1:1000. Detection was then performed using ECL Western blot chemiluminescence reagent (Pierce) and a Flourochem imaging system.

Enzyme-Linked Immunosorbent Assay

The levels of human Syndecan-2 were measured in supernatants collected from hMSCs using Enzyme-linked Immunosorbent Assay. Commercially available ELISA assays were used to measure the levels of SDC2 (CUSABIO). The assay was conducted as per the manufacturer's instructions. Calibration curves were prepared using purified standards for SDC2. Curve fitting was accomplished by sigmoidal logistic regression following manufacturer's instructions.

Isolation of Human Peripheral Blood Mononuclear Cells

To isolate peripheral blood mononuclear cells (PBMCs), anti-coagulated blood samples were collected (7-8 ml), layered onto liquid density gradient medium (GE Healthcare) and centrifuged at room temperature for 30 min at 400×g. The top layer was aspirated and discarded and PBMCs were harvested by careful pipetting of the corresponding density interface layer (buffy coat) and transferred to a fresh 50 ml tube. The PBMCs were washed twice by adding 20 ml of PBS and centrifuged for 10 min at 400×g.

This was followed by one low-speed centrifugation at 200×g for 10 min to remove platelets. The PBMCs were resuspended in T-cell culture medium (RPMI-1640, Gibco) containing 10% FBS, 50 µM β mercaptoethanol, 1% NEAA, 1% L-glutamine in Roswell Park Memorial Institute (RPMI) medium. A 10 µl aliquot of this suspension was removed and cell number determined using a haemocytometer.

Human T-Cell Proliferation Assay

Human PBMCS were washed with 0.1% BSA/PBS and stained in pre-warmed (37° C.) 10 µM Vybrant carboxyfluorescein diacetate, succinimidyl ester (CFSE)/PBS staining solution (Invitrogen) at a concentration of $2\times10^7$ cells/ml. Cells were incubated for 6 min at 37° C. protected from light and the reaction was stopped by adding 5 volumes of ice-cold medium containing 10% FBS. The PBMCs were washed three times with culture medium to remove all traces of unbound CFSE. One hundred thousand CFSE stained PBMCs were stimulated in 96-well round-bottomed plates with anti-human CD3/anti-human CD28 soluble polyclonal antibodies in T-cell medium. Various ratios of MSCs were then added to the stimulated PBMCs (1:10, 1:50, 1:100, 1:200, and 1:400). Unstimulated PBMCs were also cultured as controls. PBMCs were harvested after 4 days, after which the supernatant was removed and cells were washed in 100 µl autoMACS rinsing solution containing 2% FBS. This was followed by counterstaining with anti-human CD4+-APC. CFSE fluorescence of PBMCs was analyzed using a FACSCanto. All proliferation was analyzed and compared to stimulated PBMCs in the absence of MSC co-culture.

Results

Shed SDC2 from Supernatant of Ad.SDC2 Overexpressing MSCs is Detectable by SDC2 ELISA 24 h post-transduction with Ad.EGFP or Ad.SDC2, the medium was aspirated off and replaced with serum-free medium and collected 24, 48 and 72 h later. This supernatant was used for the SDC2 ELISA including fresh serum-free medium as a control.

Syndecans undergo regulated cleavage, usually near the plasma membrane, in a process known as shedding. Release of the syndecan extracellular domains may not only down-regulate signal transduction but also convert membrane-bound receptors into soluble effectors/or antagonists (Manon-Jensen et al., 2010).

By employing a human specific SDC2 ELISA technique we were able to detect and quantify SDC2 protein shed by huMSCs. We determined shed SDC2 protein levels in culture medium of both Ad.EGFP and Ad.SDC2 expressing MSCs. SDC2 was detected in the culture medium of Ad.EGFP cells after 48 h (346.4 pg/ml) and this increased to 689.2 pg/ml after 72 h. The SDC2-overexpressing cells exhibited elevated levels of shed SDC2 in the culture medium at 48 h (456 pg/ml), which was approx double the Ad.EGFP at 72 h (1412.7 pg/ml) (see FIG. 1).

Referring to FIG. 1, 24h post-transduction, complete medium was exchanged for serum-free (1 ml/well). Serum free supernatants were collected 48 and 72 h later. A commercially available SDC2 ELISA kit was used to detect shed SDC2 present in the supernatants. The Ad.SDC2 supernatants exhibited increased shed SDC2 amounts (~2 fold) when compared to Ad.EGFP expressing cells.

Next the SDC2 protein expression was tested to ensure serum-free medium did not affect overexpresssion.

Ad. SDC2 Overexpression Resulted

In High Levels of SDC2 Protein Expression

HuMSCs were seeded at a density of $1\times10^5$ cells/well of a 6-well plate & left to adhere for 24 h. HuMSCs were then transduced with either Ad.EGFP or Ad.S2 ($1\times10^{12}$ vp/ml).

Figure 2:
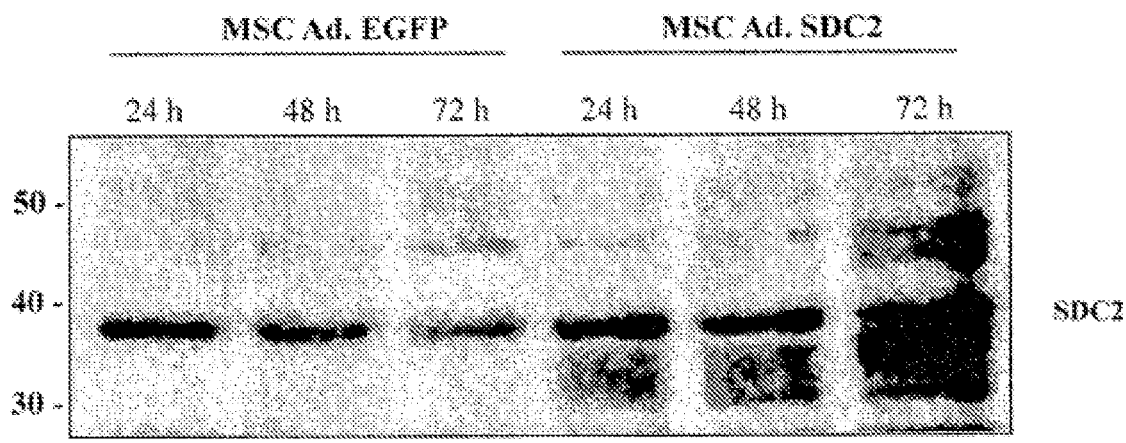
FIG. 2 shows overexpression of Ad.SDC2 results in overexpression of SDC2 protein, which increases over 72 h.

24 h post-transduction the complete medium was exchanged for serum-free medium. Protein lysates were harvested 24, 48 and 72 h later. These lysates were subjected to Western blotting for SDC2 (R&D) and it was found that SDC2 protein expression was significantly increased. We observed an increase in SDC2 bands corresponding to the molecular weight of the core protein (~25 kDa), and the dimerised form (~48 kDa) (see FIG. 2).

Immunosuppressive Potential was

Increased with the Overexpression of SDC2

Having confirmed that SDC2 protein expression was increased following Ad.SDC2 transduction, and also that the soluble form of SDC2 shed from the cell surface was also increased we investigated the effect, if any, that SDC2 overexpression would have on the immunosuppressive potential of huMSCs.

The immunosuppressive potential of Parent, Ad.EGFP and Ad.SDC2 hMSC cells was assessed using T-cell proliferation assays. Proliferation of the T-cell (CD4+) fraction of PBMCs was measured by flow cytometric analysis of CFSE expression. CFSE is a fluorescent cell staining dye used to assess cell proliferation by which its fluorescence is progressively halved with daughter cells following each cell division. Immunosuppression of the stimulated T-cells due to the presence of MSCs results in inhibition of proliferation. This was significantly reduced in the presence of Ad.SDC2 overexpressing MSCs. Results were displayed as the percentage proliferation over 3 generations. At 1:200 MSC: PBMC ratio, Ad.SDC2 MSCs showed significant T-cell immunosuppressive potential compared to the stimulated T-cell positive control (similar results were obtained using 1:10, 1:50, and 1:100 ratios). Ad.EGFP cells displayed comparable levels of T-cell immunosuppression compared to Parent MSCs (see FIG. 3).

Figure 3:
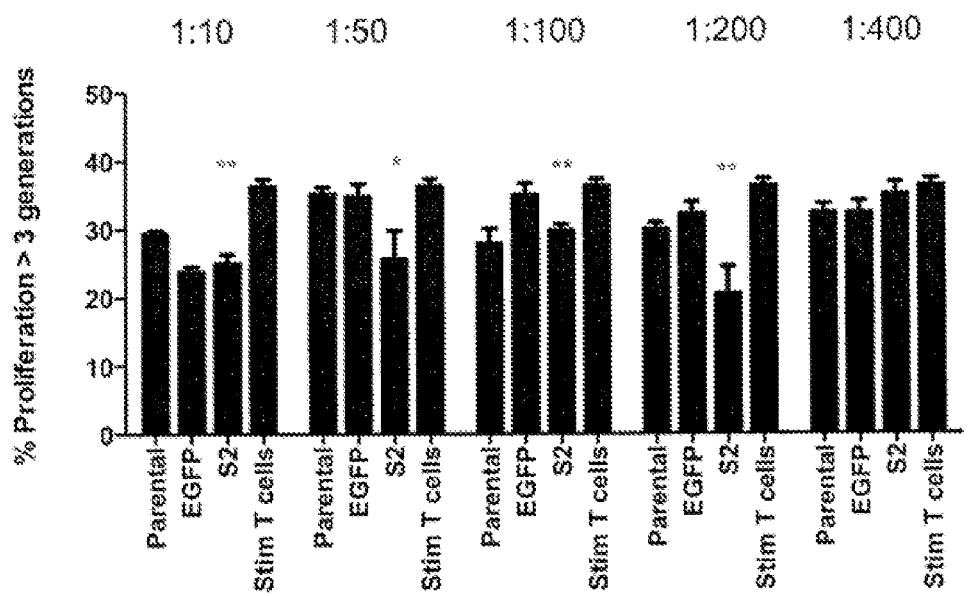
FIG. 3 shows Ad.SDC2 MSCs ("S2") had significantly increased immunosuppressive activity compared to parental MSCs.

Referring to FIG. 3, the immunosuppressive potential of Parent, Ad.EGFP and Ad.SDC2 cell populations were assessed by co-culture with stimulated T cells and quantified by flow cytometry. Results demonstrated significant immuno-suppression by Ad. SDC2 cells, which were capable of suppressing T-cell proliferation compared to the stimulated T-cell positive control. Ad.EGFP populations maintained equivalent immunosuppressive potential to parent MSCs, however Ad.SDC2 populations (marked as "S2") exhibited a significantly enhanced immunosuppressive potential to both parent and Ad.EGFP MSCs (*=P≤0.05, **=P≤0.001 as determined using Unpaired T Test).

Thus, overexpression of SDC2 in huMSCs resulted in an enhanced immunosuppressive effect when compared to parent huMSCs.

EXAMPLE 2—SUPERNATANT FROM CELLS (MSCs)

Overexpressing SDC2 Suppressed T Cell Proliferation

We assayed supernatant from a population of MSCs overexpressing SDC2 for immunosuppressive activity.

Figure 4:
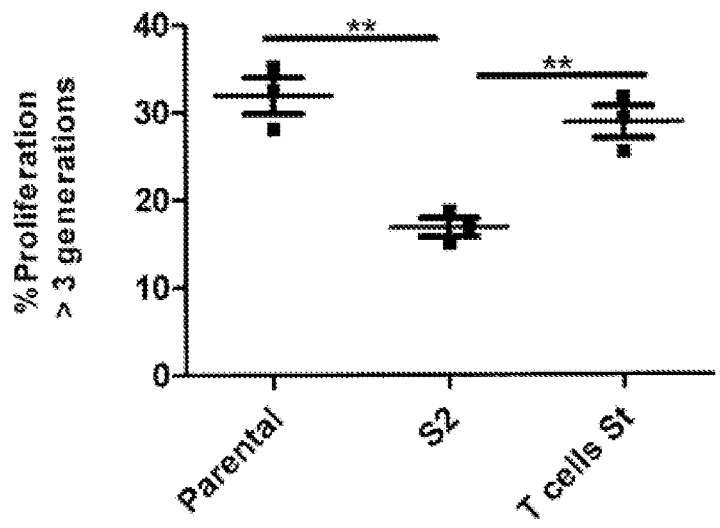
FIG. 4 shows analysis of cell culture supernatant containing SDC2 ("S2") for effect on T cell proliferation.

Referring to FIG. 4, the results showed that media from cells of the invention, namely S2-overexpressing MSCs ("S2"), was sufficient to suppress CD3/CD28 induced T-cell proliferation when compared with media from two controls: (1) Parental MSCs ("Parental"), and (2) CD3/CD28 stimulated T cells ("T cells St"). Hence, the supernatant was immunosuppressive.

EXAMPLE 3

SDC2 Assay Protocol as a Potency Assay for Therapeutic Product

We developed a protocol for product potency testing based on SDC2 assay.

The protocol comprises:
1. assay SDC2 levels in the potential product
2. compare with predetermined minimum for acceptable therapeutic product
   a. level at or above the minimum=accepted (testing ends)
   b. level below the minimum=not accepted
3. compare with maximum for an unacceptable therapeutic product
   a. level below the maximum=rejected (testing ends)
   b. level intermediate between minimum for acceptable therapeutic product and maximum for unacceptable therapeutic product=treat to increase SDC2 level, then repeat assay

EXAMPLE 4

SDC2 Assay as a Potency Assay for Therapeutic Product

We implemented the protocol of Example 3 into a specific assay for human cell preparations.

The protocol was used with the following predetermined levels:
1. we assayed SDC2 levels in the potential products
2. preparations with SDC2 levels at or above 1400 pg/ml were accepted as suitable for further processing as potential therapeutic products; preparations below that level were not accepted
3. preparations with SDC2 levels below 500 pg/ml were initially noted as not suitable for further processing
4. preparations found to be intermediate between 500 and 1400 pg/ml were identified as suitable for treatment with an SDC2 activator to increase their SDC2 levels
5. subsequently, we also noted that the preparations whose SDC2 levels were below even 500 pg/ml could be treated with an SDC2 activator to increase their SDC2 levels
6. treated populations whose SDC2 levels were raised above 1400 pg/ml were then accepted as suitable for further processing as potential therapeutic products.

EXAMPLE 5—ACTIVATION OF P53 TO INCREASE ENDOGENOUS SDC2

We tested various HDAC inhibitors for their effect on SDC2 expression on human cell populations initially isolated on the basis of SDC2 expression and maintained subsequently in culture.

Splitomicin, Valproic Acid and 2-pyrrolidinone-n-butyric acid (PBA) all increased SDC2 RNA levels at 24 hrs, with greatest stimulation by Splitomicin We similarly tested the environmental toxin benzo[a]pyrene-7,8-diol-9,10-epoxide (BPDE), and found that 600 nM BPDE increased SDC2 secretion approximately 3 fold.

EXAMPLE 6—SDC2 LEVELS IN DONOR CELL POPULATIONS 3 human MSC donors (donor cell preparations) were tested for their levels of SDC2 secretion. The results showed that two donors identified as good performers (labelled as donors 109 and 110) had high levels of SDC2 whereas a third donor identified as a poor performer (donor 111) had low SDC2 levels, and failed the SDC2 assay of Example 4.

EXAMPLE 7

Comparison of Topical Administration of SDC2+, SDC2− And PA-SSC in Diabetic Wound Healing We compared the activity of various stem cell populations in a wound healing model using Excellagen® (a highly purified formulated homogenate of fibrillar bovine Type I collagen).

In Vivo Experimental Model

Male New Zealand white rabbits (3-3.5 kg) were used for the study. Diabetes was induced in these rabbits with by administration of Alloxan (150 mg/kg) via a marginal ear vein. Serum blood glucose was checked daily using Accu-check advantage strips (Roche). After 5 weeks of hyperglycemia, rabbits were anesthetized using xylazine and ketamine. Sterile, disposable 6-mm punch biopsies were used to create five wounds (three wounds on one ear and two wounds on the other ear). Each wound was treated with one of five randomized treatment groups:

| | |
|---|---|
| 1 | No treatment |
| 2 | Excellagen ® scaffold alone (25 µl); |
| 3 | Excellagen ® with 1 × 10$^6$ wild type MSCs (25 µl soln from cell pellet resuspended in Excellagen ®) |
| 4 | Excellagen ® with 1 × 10$^6$ SDC2 positive ("SDC2+") type MSCs (25 µl soln from cell pellet resuspended in Excellagen ®) and |
| 5 | Excellagen ® with 1 × 10$^6$ SDC2 negative ("SDC2−") type MSCs (25 µl soln from cell pellet resuspended in Excellagen ®). |

After application of treatment, the wounds were covered with a polyurethane dressing (OpSite; Smith & Nephew), and the ear was stitched and covered with adhesive dressing (Operfix; Promedicare, Clonee, Ireland) until day 7. The study treatments were randomised and blinded for unbiased assessment. After 7 days, rabbits were sacrificed with intravenous sodium pentobarbital (2 mL).

Result Analysis

After one week of treatment, there was significant difference in wound healing within the different treatment groups. Each wound was traced on the day of sacrifice. A fresh wound was made on the day of sacrifice and the percentage wound area reduction over 1 week was calculated.

Percentage Wound Closure Assessment

On the day of sacrifice, each wound was traced six times. The area of each image was measured using Cell B software (Olympus), and the average area was calculated. The percentage wound area reduction over 1 week in each treatment group was calculated.

Percentage Wound Closure

The percentage wound closure analysis revealed that Excellagen® accelerated the wound healing rate as compared to untreated wounds. Wounds treated with 1 million SDC2+ cells in Excellagen® scaffold showed highest and most significant percentage wound closure when compared with untreated group at 1 week. The wound closure effect of Excellagen® was significantly augmented when mixed with SDC2+ cells.

All wound sections were further processed for histology and stereological analysis.

Histology

The wounds were cut across the midline and fixed in 10% formalin for 24 h. The tissue was processed using a tissue processor (ASP300; Meyer Instruments, Houston, Tex.) and embedded in paraffin. Sections (5 mm) were stained with hematoxylin and eosin and Masson's trichrome using standard protocols.

From the histology staining, it could be observed that Excellagen® treated wounds showed good wound healing with formation of new tissue on wound site. The wounds treated with SDC2+ cells mixed with Excellagen® showed most effective wound healing. The mixing of SDC2+ cells augmented the healing potential of Excellagen® alone. When compared with no treatment group, SDC2+ treated wound showed formation of new tissue on wound site with collagen formation at base of the wound bed.

Neovasculature in the Wound Bed with SDC2+ Cells Treated Wounds

MSCs are known to promote angiogenesis in addition to improving cutaneous wound healing. A similar effect was observed in wounds treated with SDC2+ cells. In these wounds, formation of new blood vessels could be observed within the wound bed. Hence, significant wound healing was observed in SDC2+ treated wounds by increased percentage wound closure and may be associated with more efficient neovasculature.

Summary

MSCs mixed with Excellagen® retained good metabolic activity reflecting no adverse effect of the Excellagen® matrix on viability of cells. Cells were densely populated throughout the Excellagen® matrix with proper distribution and without any cell clump formation. In the current study, the wounds treated with SDC2+ cells mixed with Excellagen® showed increased percentage wound closure when compared with Excellagen® treated control alone. The SDC2+ cells significantly augmented the wound healing potential of Excellagen®. MSCs are also reported to promote angiogenesis. In the present study, increased blood vessel formation was observed within the wound bed in SDC2+ cells treatment group. Hence, SDC2+ treated wounds showed significant wound healing benefit by increased percentage wound closure with more prominent neovasculature. Thus, the SDC2+ cells of the invention in a matrix showed improved wound healing potential with less healing time.

EXAMPLE 8—CANCER CELL MIGRATION

Cell migration is a critical parameter for in vitro cell culture-related studies. It is necessary to monitor the dynamic changes of cell populations under different conditions. Using a real time cell analyser (RTCA, xCELLigence, Roche) which is an impedance-based device we can monitor the following properties in real time: proliferation, migration and cell adherence. Such properties are involved in cancer evolution. We used this method to establish the migratory capacity of cancer cells toward conditioned medium. The model is accepted as predictive of efficacy in cancer therapy—reduced migration in the model indicates anti-cancer properties.

In our investigations, cell migration was determined using 16-well CIM plates read in real-time using the aforementioned xCELLigence device. For these studies a variety of cancer cell lines were used from breast cancer (MDA-MB-231, MDA-MB-486, MCF-10A), prostate cancer (DU145), pancreas cancer (SU-86-86) and colon carcinoma (HCT116).

The results are summarised in Table 1:

TABLE 1

| | Cancer Cell Migration | | | |
| --- | --- | --- | --- | --- |
| | Recombinant SDC2 Amount | | | |
| Cell Type | 100 ng/ml | 500 ng/ml | 1000 ng/ml | Ad. SDC 2 (3 µl) |
| MDA-MB-231 | ↓↓ | ↓↓↓↓— | | ↓↓↓ |
| MDA-MB-486 | | | | ↓ |
| MCF-10A | | | | — |
| Du145 | | ↓— | | ↓ |
| SU-86-86 | ↓↑ | ↓↓ | ↓↑ | ↓ |
| HCT116 | ↓ | ↓ | ↓ | |

Key:
↑ = increased migration compared to conditioned media;
↓ = decreased cell migration compared to conditioned media;
— = no changed compared to conditioned media.

Breast Cancer Cell Lines
   Recombinant SDC2 (500 ng/ml rSDC2 (n=5) and 100 ng/ml (n=2)) inhibited migration of MDA-MB-231 cells. A similar migratory result was produced with Ad.SDC2 (3 µl)-CM (n=3).
   MDA-MB-486 cells exhibited a reduction in migration towards Ad.SDC2-CM (3 µl; n=1).
   Ad.SDC2 (3 µl) did not alter migration of MCF-10A cells (n=1).
Prostate Cancer Cell Lines
   The addition of 500 ng/ml of rSDC2 to the serum free MSC-CM reduced migration of DU145 cells in one experiment and no change in a second experiment when compared to conditioned media alone. Ad.SDC2 (3 µl) reduced migration of DU145 cells (n=1). This shows that the EC domain of SDC2 inhibited migration of this prostate cancer cell line.
Pancreatic Cancer Cell Line
   The migratory capacity of SU-86-86 cells varied; one experiment increased migration towards rSDC2-CM (at 100 ng/ml, 500 ng/ml and 1000 ng/ml; n=1) and another showed a decrease in migration towards rSDC2-CM (at 100 ng/ml, 500 ng/ml and 1000 ng/ml; n=1).
Colon Carcinoma Cell Line
   HCT116 cells showed a decrease in migration towards rSDC2-CM at all concentrations tested (100-1000 ng/ml).

Conclusion

Overall, these results show the changes in behaviour of different cancer cells towards SDC2 in the media. In general, SDC2 reduced the migratory capacity of cancers, indicating an anti-cancer effect in the model, in particular MDA-MB-231 cells (breast cancer).

In initial tests, to be confirmed by a subsequent, expanded programme of work in this area, an antibody to SDC2 showed a similar inhibition of breast cancer migration, indicating anti-cancer activity.

EXAMPLE 9—IMMUNE SUPPRESSION

Using rSDC2 as used in Example 8, we investigated the activity of SDC2 in a model of immune suppression. We found that SDC2 protein suppressed NFκB activation by TNFα and IL1β. This demonstrated immune suppressing activity in the SDC2 protein per se.

Figure 5:
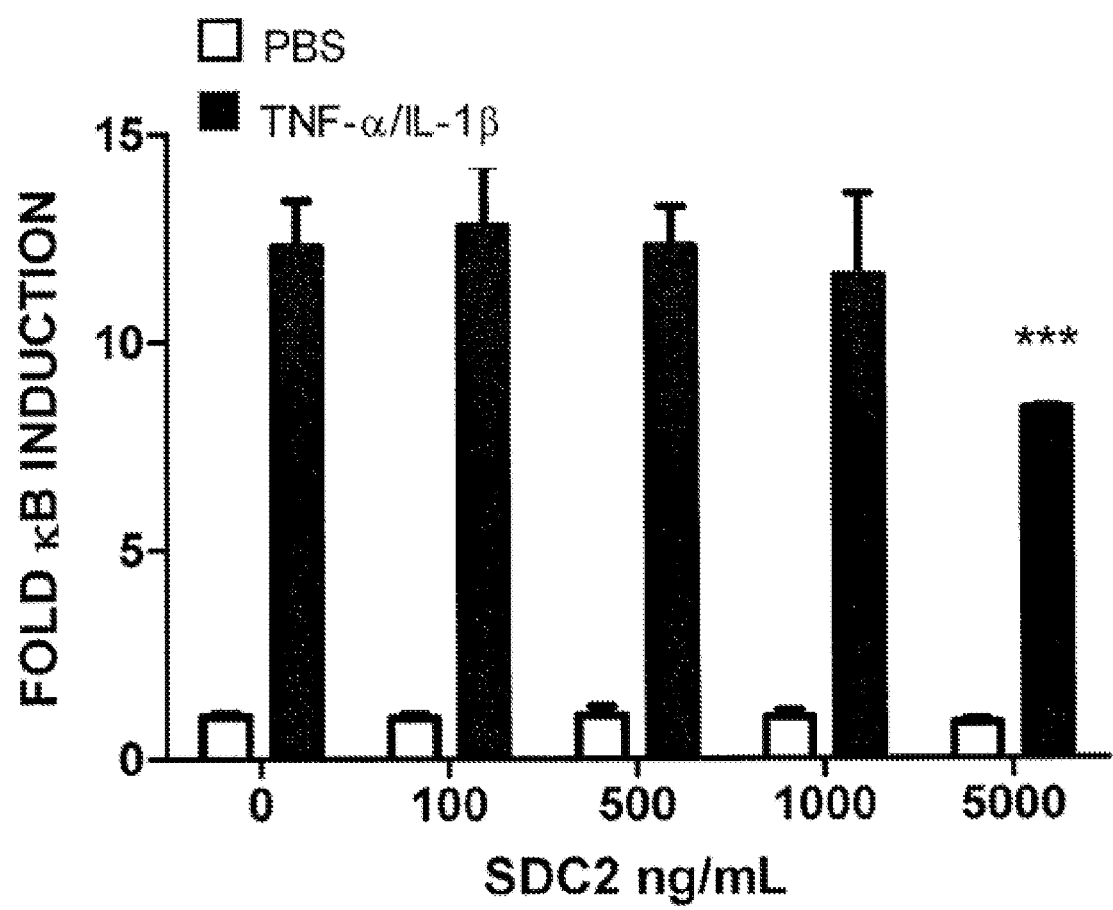
FIG. 5 shows SDC2 protein suppresses NFκB activation by TNFα and Up.

A549 cells stably transduced with κB luciferase plasmid were pretreated for 1 hour with SDC2 recombinant protein. 10 ng/mL TNF-α/IL-1β was added to the media and luciferase assay performed after 24 hours. The results are shown in FIG. 5. ***=p<0.0001 with respect to 0 ng/mL S2

Figure 6A:
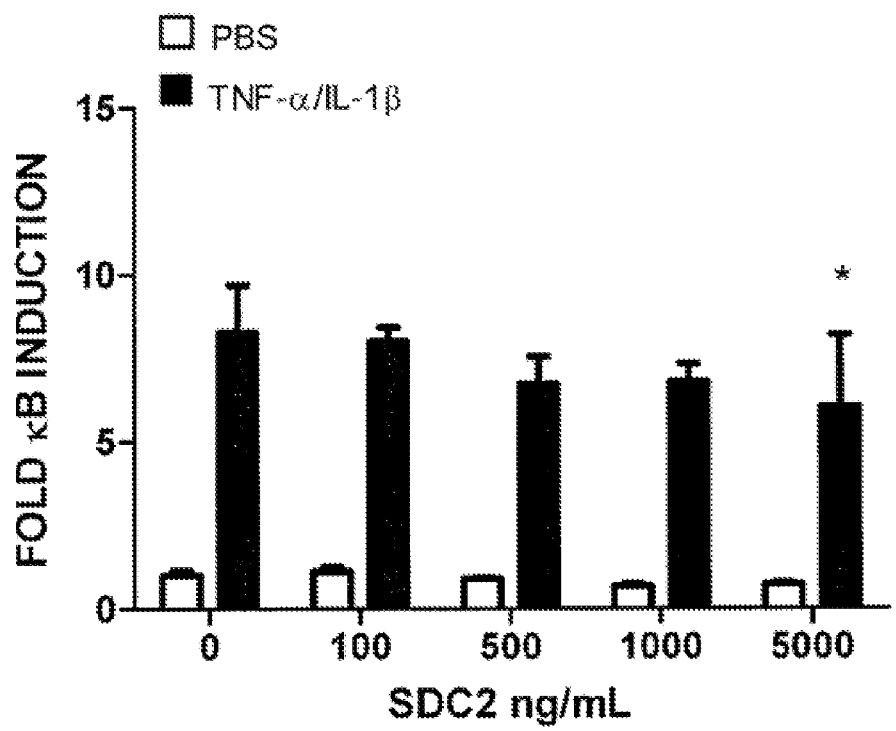
FIG. 6A and FIG. 6B show NFκB induction in response to recombinant SDC2 and activation by TNFα and IL1β.
Figure 6B:
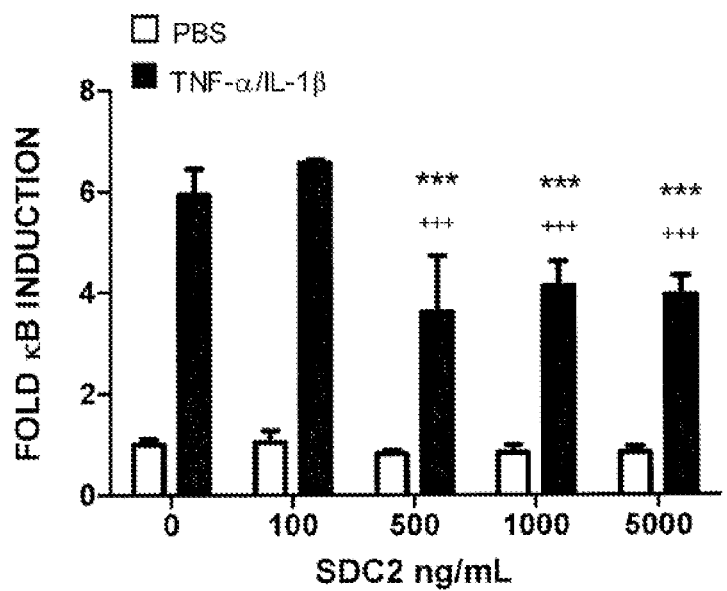

A549 cells stably transduced with KB luciferase plasmid and treated for 24 hours with recombinant SDC2. The results are shown in FIG. 6A and FIG. 6B. In the top panel: cytokines were added to the media for 24 hours and luciferase assay performed. In the bottom panel: media was replaced before addition of cytokines for 24 hours. *=p<0.01 with respect to 0 ng/mL S2; ***=p<0.0001 with respect to 0 ng/mL S2; +++=p<0.0001 with respect to 100 ng/mL S2.

Figure 7A:
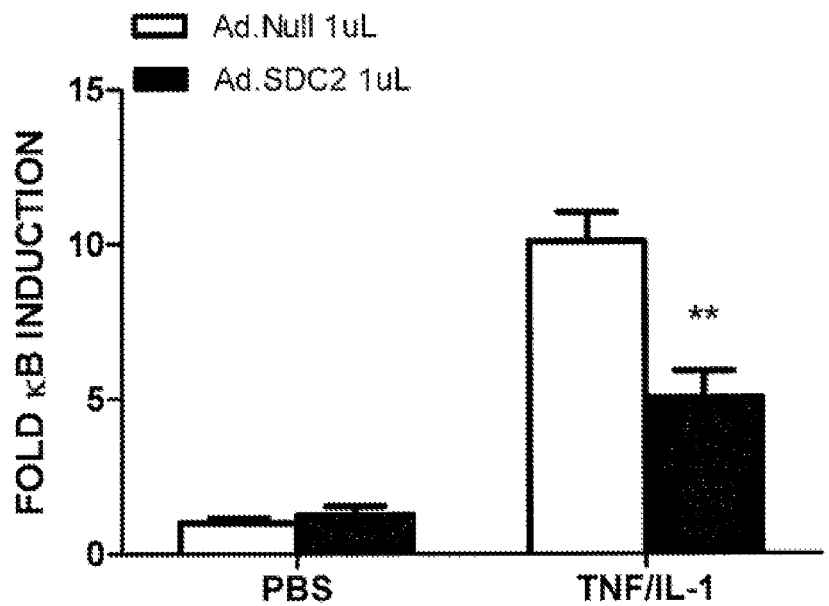
FIG. 7A and FIG. 7B show NFκB induction in response to overexpression of SDC2 following activation by TNFα and IL1β.
Figure 7B:
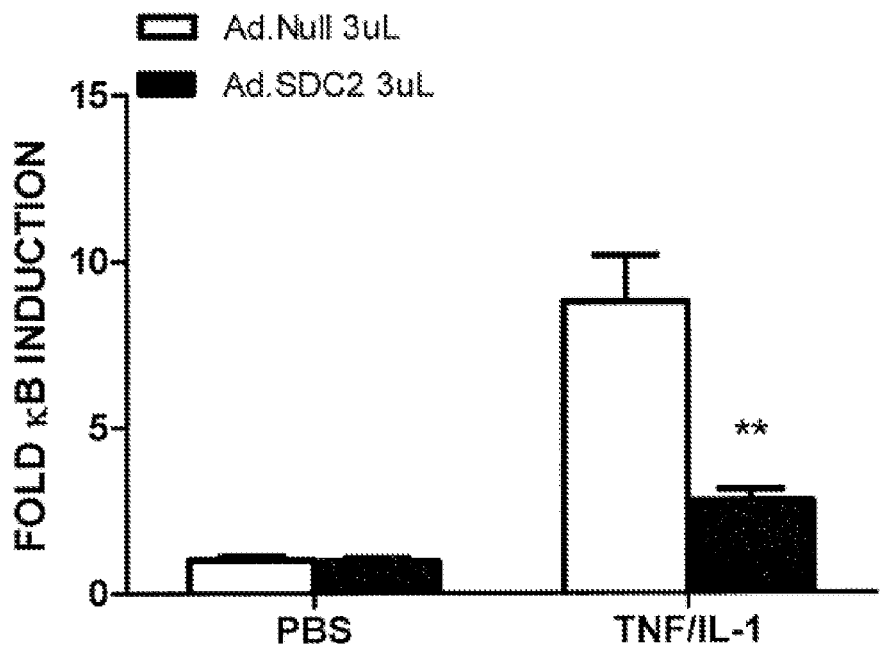

A549 κBL cells were transduced with either 1 μL/mL or 3 μL/mL Ad.Null or Ad.SDC2 and treated with cytokines for 24 hours before luciferase assay performed. The results are shown in FIG. 7A and FIG. 7B. **=p<0.001 with respect to 0 ng/mL S2.

These results showed an immune suppression effect of SDC2 protein.

EXAMPLE 10—P53 REGULATION OF SDC2

To determine the role of p53 in SDC2 protein signaling we pharmacologically perturbed the p53 pathway within the MSC by utilising a p53 agonist (nutlin-3a) to help dilineate the SDC2 response. Nutlin-3a induces pronounced p53 response and inhibits growth.

Methods
Cell Culture and Treatment

MSCs were plated at a density of $10^5$ cells per well of a 6-well plate (Nunc) in complete media (α-MEM, 10% FBS) and left to adhere overnight. Medium was then exchanged for serum-free containing Nutlin-3a or DMSO as a carrier control. 24 h post-induction the cells were harvested for both RNA and protein and the serum-free supernatant was collected for ELISA.

Enzyme-Linked Immunosorbent Assay (ELISA)

The levels of human Syndecan-2 was measured in supernatants collected from hMSCs using commercially available ELISA assays (CUSABIO). The assay was conducted as per the manufacturer's instructions. Calibration curves were prepared using purified standards for SDC2. Curve fitting was accomplished by sigmoidal logisitic regression following manufacturer's instructions.

Results
Nutlin-3a Treatment of MSCs Results in a Dose-Dependent Increase in SDC2 Shedding 24 h post-treatment with Nutlin-3a (5, 10, 20 μM) or DMSO carrier control (5, 20 μM), the supernatant from MSCs was collected, centrifuged for 5 min at 1500 rpm and subjected to SDC2 ELISA including unconditioned serum-free media as an additional control.

Figure 8:
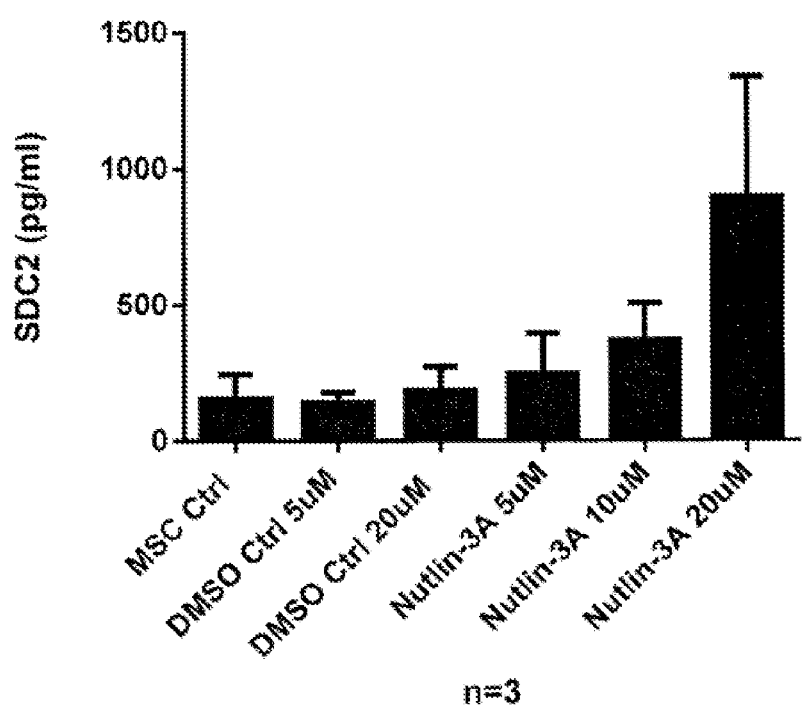
FIG. 8 shows nutlin-3a treatment of MSCs causes a dose-dependent increase in SDC2 shedding.

FIG. 8 shows that Nutlin-3a treatment of MSCs causes dose-dependent increase in SDC2 shedding. MSCs treated with either Nutlin-3a or DMSO as a carrier control for 24 h in serum-free media. The serum-free supernatants were collected and a commercially available SDC2 ELISA kit was used to detect shed SDC2 present in the supernatants. The Nutlin-3a treated cells exhibited increased SDC2 shedding when compared to the DMSO control.

FIG. 8 is representative of three independent experiments with three different human MSC donors. The amount of shed SDC2 increases from 250 pg/ml in the 20 μM DMSO control to an average of nearly 1000 pg/ml in the Nutlin-3a 20 μM dose.

Thus this experiment demonstrates that a compound that upregulates p53 activity (Nutilin-3a) also increases SDC2 shedding.

EXAMPLE 11

Chemotherapeutics Enhance SDC2 Shedding from Human MSCs

We tested various chemotherapeutics inhibitors for their effect on SDC2 shedding from human MSCs; in particular taxol, camptothecin, etoposide and BPDE (benzo(a)pyrene diolepoxide).

MSCs were treated with the chemotherapeutics for 24 h prior to serum starve for 24 h. The cell supernatant were harvested and the relative fold change in shed SDC2 protein expression was analysed by ELISA.

Figure 9:
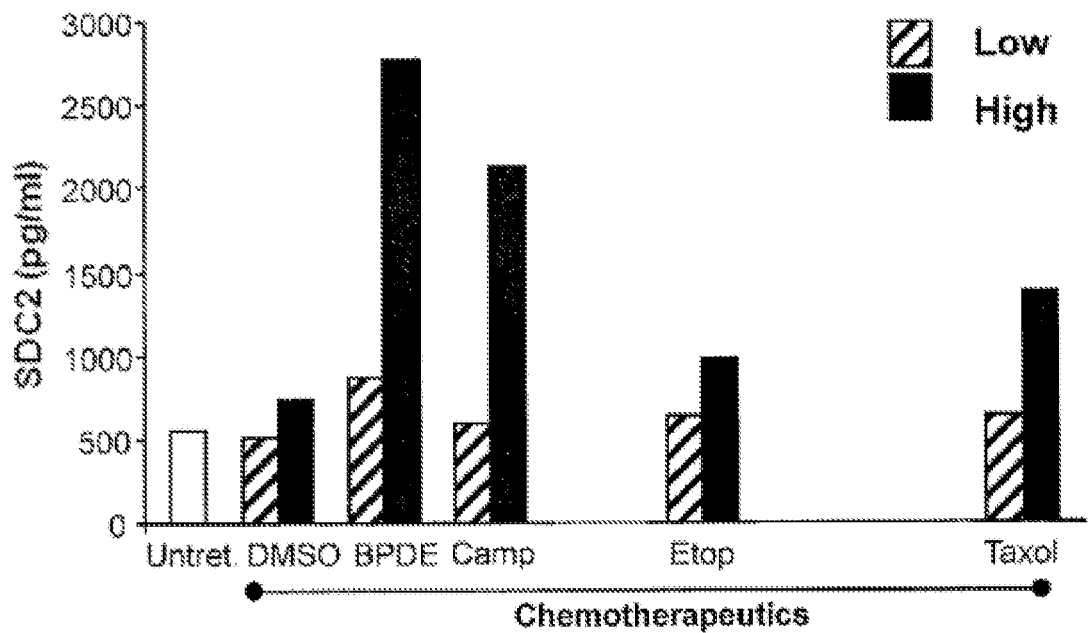
FIG. 9 shows chemotherapeutics enhance SDC2 shedding from human MSCs.

FIG. 9 shows the results of these experiments and that chemotherapeutics enhance SDC2 shedding from human MSCs.

EXAMPLE 12

Identifying Domains of SDC-2 Responsible for Regulation of NF-κB

To determine which fragment or domains of SDC-2 could be responsible for regulation of NF-κB signaling we used a luciferase reporter gene system under the control of a κB motif. We transduced these cells with an empty vector control adenovirus (p3×FLAG-CMV-14) or a vector expressing 12 fragments of SDC2 (1.4 to 12.4) and determined the effect on NF-κB transcriptional activity.

Figure 10:
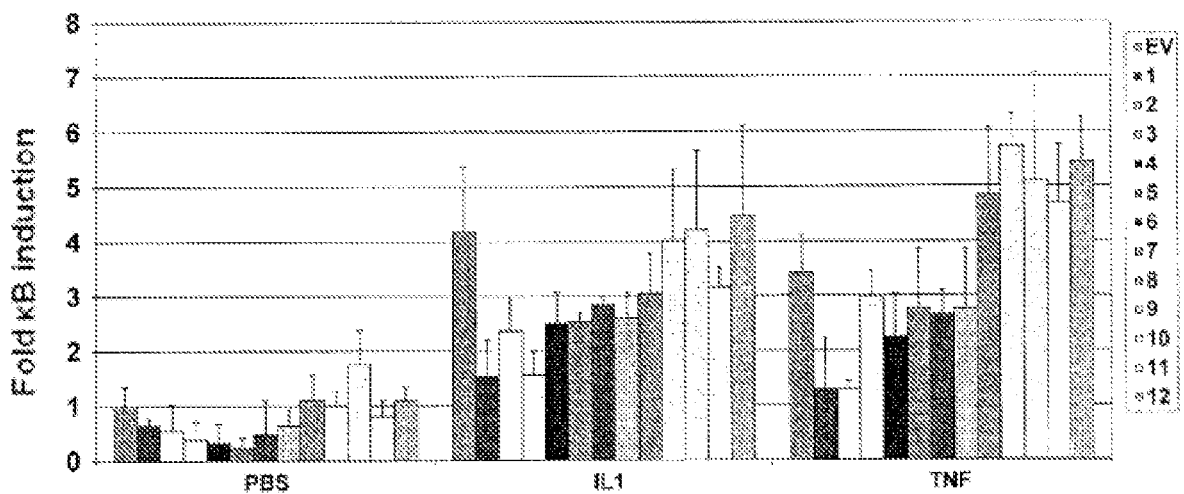
FIG. 10 shows over-expression of SDC-2 C-terminal deletion fragments (1-6) attenuates NF-κB activity in response to IL-1β or TNF-α.

FIG. 10 shows that over-expression of SDC-2 C-terminal deletion fragments (1-6) attenuate NF-κB activity in response to IL-1β, or TNF-α. NF-κB-luciferase expressing cells were transfected with Empty vector (p3×FLAG-CMV-14) or vector expressing fragments 1.4 to 12.4. After 24 hrs, cells were treated with cytokines for 24 hrs, IL-1β (10 ng/ml), TNF-α (10 ng/ml), then a luciferase assay was performed.

The fragments are referred to in FIG. 10 as numbers 1 to 12. These correspond to the following peptide fragments of SDC-2: 1, 1-79; 2,1-87; 3,1-100; 4,1-144; 5,1-169; 6,1-201; 7,19-79; 8,19-87; 9,19-100; 10,19-144; 11,19-169; 12,19-201

Pro-inflammatory cytokines such as TNF-α and IL-1β, can activate NF-κB transcriptional activity, which is observed in empty vector control lanes. NF-κB transcriptional activity is induced approximately, 3-, and 4-fold by TNF-α and IL-1β respectively in control cells. However, in the fragment 1-6 expressing cells the TNF-α-, IL-1β-, and TNFα/IL-1β-induced increase in NF-κB transcriptional activity is significantly reduced (FIG. 10). Notably, the fragments expressing the N-terminal signal peptide (1-18) significantly inhibited both IL1β and TNF-α activation of NF-κB. Fragments 1.4 (1-79) and 2.4 (1-87) robustly inhibited NF-κB activation, suggesting the heparan sulfate binding sites and signal peptide are both required for the suppression of NFκB.

This data suggests that the immunosuppressive properties of SDC2, and possibly the migratory properties, could be attributed to the N-terminus of SDC-2. By inhibiting NF-κB activity, SDC2 fragments can reduce the immune response and be used as anti-inflammatory agents, and for wound healing, cancer therapy and inflammatory disease.

EXAMPLE 13

Syndecan-2 Inhibits NF-kB Signaling and Limits IL6 and IL8 Secretion in Response to IL-1β, TNFα, and IL 1β/TNFα

Figure 11A:
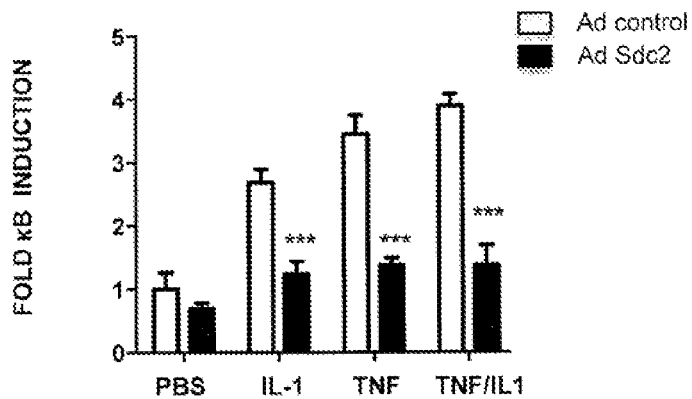
FIG. 11A, FIG. 11B, and FIG. 11C show adenoviral expression of SDC-2 attenuates NF-κB activity and IL6/IL8 secretion in response to IL-1β, TNFα and IL-1β/TNFα.

To determine whether SDC-2 could be affecting NF-κB signaling we used a luciferase reporter gene system under the control of a κB motif. We transduced these cells with an empty vector control adenovirus (Ad-control) or an SDC2 expressing adenovirus (Ad-SDC2) and determined the effect on NF-κB transcriptional activity. Pro-inflammatory cytokines such as TNFα, IL-1β, and a combination of TNFα/IL-1β can activate NF-κB transcriptional activity, as shown in FIG. 11A. NF-κB transcriptional activity is induced approximately, 3-, 3.5-, and 4-fold by TNFα, IL-1β, and TNFα/IL-1β respectively in control cells. However, in SDC-2 expressing cells the TNFα-, IL-1β-, and TNFα/IL-1β-induced increase in NF-κB transcriptional activity is significantly reduced (FIG. 11A, FIG. 11B, and FIG. 11C).

Figure 11B:
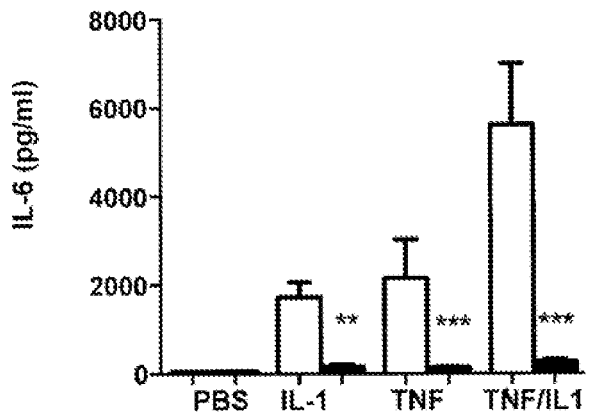
Figure 11C:
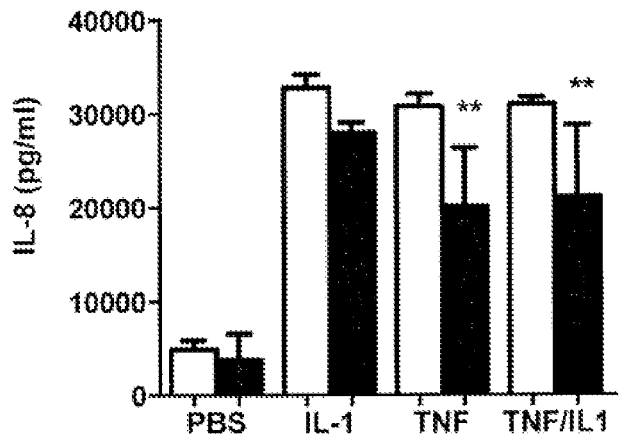

In addition to the decrease in NF-κB transcriptional activity, there was an associated significant decrease in TNFα-, IL-1β-, and TNFα/IL-1β-induced release of IL-6 and IL-8, both of which are regulated by NF-κB (FIG. 11B and FIG. 11C).

Taken together this data shows the anti-inflammatory properties of SDC2, by regulation of the NF-κB pathway.

EXAMPLE 14

Targeting of SDC2 Antibodies to SDC2 Localised in Cancer Stroma

We investigated the localisation of SDC2+ cells in a cancer model to confirm earlier work and determine a strategy for therapeutic intervention in cancer treatment.

An MMTV PyMT-P2A-mCherry-P2A-OVA (PyMT ChOVA) mouse was kindly generated by Prof. Matt Krummel at UCSF. Where the mCherry and OVA (ovalbumin) sequence is linked to the polyoma virus, middle T antigen (PyMT) and the whole sequence is driven by the MMTV (mouse mammary tumor virus) promoter.

Tumour Growth—

Female PyMT ChOVA mice were monitored for tumour onset by palpation of mammary glands and monitored weekly for total tumour burden by measurement of tumour size with Vernier calipers. Combined tumour burden was calculated by summation of all palpable tumour areas. Tumour area was defined as length×width of tumour. Mice were sacrificed when tumour burden exceeded 200 mm$^2$, in accordance with ACREC animal protocol.

Tumour Digestion—

PyMT tumours were dissected from mice and total weight of removed tumour was determined. Tumours were then minced using scalpels and digested with 2 mg/ml Collagenase IV (Sigma) and 200 pg/ml DNAse per 0.3 grams of tumour weight for 1.5 hrs. Tumour was then passed through a 100 μm cell strainer to remove large pieces of undigested tumour. A 70%/37%/30% Percoll gradient was then run to remove dead cells and red blood cells, and both interfaces were collected.

Flow Cytometry—

All antibodies were purchased from R&D Systems, BD Pharmingen, eBioscience, Invitrogen or Biolegend. For surface staining, cells were incubated with anti-Fc receptor antibody (24G2) and stained with the appropriate antibodies in PBS 2% FCS. All flow cytometry was performed on a FACSCanto flow cytometer (BD Biosciences). Analysis of flow cytometry data was done using FlowJo (Treestar).

Tumour stromal cells were sorted based on the following markers CD45$^-$, mCherry$^-$, gp38$^+$, CD362$^+$ and DAPI$^-$. Epithelial tumour cells were sorted based on being CD45$^-$, DAPI$^-$ and mCherry$^+$.

The results showed that SDC2 (CD362/Syndecan-2) protein expression was localised to CD45$^-$, mCherry$^-$, gp38$^+$, CD362$^+$ and DAPI tumour stroma. Thus, SDC2-positive cells were localised in the cancer stroma, further supporting earlier work indicating an anti-cancer effect of SDC2 antagonists, e.g. antibodies to SDC2, in cancer therapy.

The invention hence provides immunomodulation and other therapies via modulation of SDC2 levels and/or activity.

The invention claimed is:

1. A method of reducing an inflammatory response in a subject, the method comprising contacting a cell of the subject with a composition comprising Syndecan-2 (SDC2) or a fragment of SDC2, wherein the SDC2 or the fragment of SDC2 has an anti-inflammatory effect.

2. The method of claim 1, wherein the fragment of SDC2 comprises at least 30 consecutive residues of the amino acid sequence of SEQ ID NO: 3.

3. The method of claim 1, wherein the SDC2 or fragment of SDC2 has a sequence with at least 90% identity to the amino acid sequence of SEQ ID NO: 3 over at least 30 consecutive residues.

4. The method of claim 1, wherein the fragment of SDC2 comprises at least 61 consecutive residues of the amino acid sequence of SEQ ID NO: 3.

5. The method of claim 1, wherein the fragment of SDC2 comprises at least 79 consecutive residues of the amino acid sequence of SEQ ID NO: 3.

6. The method of claim 1, wherein the fragment of SDC2 comprises at least 87 consecutive residues of the amino acid sequence of SEQ ID NO: 3.

7. The method of claim 1, wherein the SDC2 has the amino acid sequence of SEQ ID NO: 3.

8. The method of claim 1, wherein the fragment of SDC2 is a polypeptide selected from the group consisting of residues 1-79; 1-87; 1-100; 1-144; 1-169; 9-79; 19-87; 19-100; 19-169; and 19-201 of a full-length SDC2.

9. The method of claim 1, wherein the SDC2 is human SDC2.

10. The method of claim 1, wherein the SDC2 or fragment of SDC2 is obtained from a cell culture supernatant.

11. The method of claim 1, wherein the composition comprises a cell.

12. The method of claim 11, wherein the cell comprises a stromal stem cell.

13. The method of claim 11, wherein the cell comprises a nucleic acid encoding the SDC2 or fragment of SDC2.

14. The method of claim 11, wherein the cell is transfected with a vector that encodes the SDC2 or fragment of SDC2.

15. The method of claim 11, wherein the cell is infected with a virus that encodes the SDC2 or fragment of SDC2.

16. The method of claim 1, wherein the composition further comprises an anti-inflammatory agent selected from the group consisting of an anti-TNFα antibody, infliximab, adalimumab, certolizumab, golimumab, etanercept, an anti-CD3 antibody, muromonab-CD3, otelixizumab, teplizumab, visilizumab, and combinations thereof.

17. The method of claim 1, wherein the SDC2 or fragment of SDC2 reduces at least one symptom of an inflammatory response in the subject.

18. The method of claim 1, wherein the inflammatory response comprises a T cell proliferation response.

19. The method of claim 1, wherein the inflammatory response comprises NFκB activation.

20. The method of claim 1, wherein the inflammatory response comprises a response to at least one of Tumor Necrosis Factor-α (TNFα), Interleukin-6 (IL6), Interleukin-8 (IL8), and Interleukin-1β (IL1 (3).

* * * * *

SEQUENCE LISTING

<160> NUMBER OF SEQ ID NOS: 4

<210> SEQ ID NO 1
<211> LENGTH: 3491
<212> TYPE: DNA
<213> ORGANISM: Homo sapiens

<400> SEQUENCE: 1

```
gcccggagaa gcaggctcag gagggaggga gccagaggaa aagaagagga ggagaaggag      60
gaggacccgg ggagggaggc gcggcgcggg aggaggaggg gcgcagccgc ggagccagtg     120
gccccgcttg gacgcgctgc tctccagata cccccggagc tccagccgcg cggatcgcgc     180
gctcccgccg ctctgcccct aaacttctgc cgtagctccc tttcaagcca gcgaatttat     240
tccttaaaac cagaaactga acctcggcac gggaaggag tccgcggagg agcaaaacca      300
cagcagagca agaagagctt cagagagcag ccttcccgga gcaccaactc cgtgtcggga     360
gtgcagaaac caacaagtga gagggcgccg cgttcccggg gcgcagctgc gggcggcggg     420
agcaggcgca ggaggaggaa gcgagcgccc ccgagcccg agcccgagtc cccgagcctg     480
agccgcaatc gctgcggtac tctgctccgg attcgtgtgc gcgggctgcg ccgagcgctg     540
ggcaggaggc ttcgttttgc cctggttgca agcagcggct gggagcagcc ggtccctggg     600
```

```
gaatatgcgg cgcgcgtgga tcctgctcac cttgggcttg gtggcctgcg tgtcggcgga      660
gtcgagagca gagctgacat ctgataaaga catgtacctt gacaacagct ccattgaaga      720
agcttcagga gtgtatccta ttgatgacga tgactacgct tctgcgtctg gctcgggagc      780
tgatgaggat gtagagagtc cagagctgac aacatctcga ccacttccaa agatactgtt      840
gactagtgct gctccaaaag tggaaaccac gacgctgaat atacagaaca agatacctgc      900
tcagacaaag tcacctgaag aaactgataa agagaaagtt cacctctctg actcagaaag      960
gaaaatggac ccagccgaag aggatacaaa tgtgtatact gagaaacact cagacagtct     1020
gtttaaacgg acagaagtcc tagcagctgt cattgctggt ggagttattg ctttctctt      1080 tgcaattttt cttatcctgc tgttggtgta tcgcatgaga aagaaggatg aaggaagcta     1140
tgaccttgga gaacgcaaac catccagtgc tgcttatcag aaggcaccta ctaaggagtt     1200
ttatgcgtaa aactccaact tagtgtctct atttatgaga tcactgaact tttcaaaata     1260
aagcttttgc atagaataat gaagatcttt gttttttgtt ttcattaaag agccattctg     1320
gcactttaat gataaaatcc cattgtattt aaaacatttc atgtatttct ttagaacaac     1380
ataaaattaa aatttaacat ctgcagtgtt ctgtgaatag cagtggcaaa atattatgtt     1440
atgaaaaccc tcgatgttca tggaattggt ttaaacttt atgcgcaaat acaaaatgat      1500 tgtcttttc ctatgactca aagatgaaag ctgtttcatt tgtgtcagca tgtctcagat      1560
tgaccttacc aagttggtct tactttgtta atttatctgt tgtccccttc ctctcctctg     1620
ccctcccttc ttgtgccctt aaaaccaaac cctatgcctt ttgtagctgt catggtgcaa     1680
tttgtctttg gaaaattcag ataatggtaa tttagtgtat atgtgatttt caaatatgta     1740
aactttaact tccactttgt ataaattttt aagtgtcaga ctatccattt tacacttgct     1800 ttattttca ttacctgtag ctttgggcag atttgcaaca gcaaattaat gtgtaaaatt      1860
ggattattac tacaaaaccg tttagtcata tctatctaat cagatcttct tttgggagga     1920
tttgatgtaa gttactgaca agcctcagca aacccaaaga tgttaacagt attttaagaa     1980
gttgctgcag attcctttgg ccactgtatt tgttaatttc ttgcaatttg aaggtacgag     2040
tagaggttta aagaaaaatc agttttttgtt cttaaaaatg catttaagtt gtaaacgtct     2100
ttttaagcct ttgaagtgcc tctgattcta tgtaacttgt tgcagactgg tgttaatgag     2160
tatatgtaac agtttaaaaa aaagttggt attttataag cacagacaat tctaatggta      2220
acttttgtag tcttatgaat agacataaat tgtaatttgg gaacataaaa actactgaat     2280
aaatcatgtg gcctaatatt gaaaatgtca ctgttataaa ttttgtacat ttttgatcaa     2340
atgtacatct cccctttgct aacggccgtc tgctctcaag gatgacgtgg gtttgatttc     2400
taagtgtttc acagtgtctg taaatcaaga ccaaagagcc tgtcgatgag actgtttatt     2460
accagattca cttctgaatt ggccagagga atctgaatg tattatcctg tgtgtgtcta      2520
ggtagagata ttgaaggct gccagggat ttcgaagttt gcaacccttta taggataact       2580 gatggcaata ttaagacaga cgcctgcttt tgcaaataac ttacaagact gtaaattcca     2640
aagatctgaa tggggctttc ctgatgttgg tatctaaggc ttaggcctat agattgattt     2700 accttttggaa ttgtgctcca aatgtctact gaagcttaac cgaagaacta ataaatggac    2760
tacagtagct cacgttacag ggaaggaggg taggcaggga ggctctgtgt gttaaaatga     2820
gggtctcact gctttaggat tgaagtggct ggaaagagtg atgcctgggg aaggagatgg     2880
agttatgagg gtactgtggc tggtactttc tgtactaaac atttccttttt tctatttac     2940
```

-continued

| | |
|---|---|
| cactaattttt gttttaaact gtgagccgtc caagtcagaa gaagacagca aaaaaagcaa | 3000 |
| cttttccaac atacaattta cttttaataa agtatgaata tttcattttg agaacattcc | 3060 |
| ctggaattgc cacataattc attaaaaaca ttttttttaag caacacttgg aacagtgttt | 3120 |
| actttaaatc cttaatggcc ttaattaatt ctcagattcc tgccccatca cttacagaac | 3180 |
| caattcactt tagagtgact aaaaggaaac gatagcctag ctttctaaag ccacgctgtg | 3240 |
| tccctcaatt acagagggta ggaatgggta tacctctaac tgtgcaaagc agagtgaaat | 3300 |
| tcaattcata gaataacaac tgctgggaat atccgtgcca ggaaaagaaa aatttctggc | 3360 |
| aaatattttg tcactgctgt aaagcaaaat atttgtgaaa gtgccaaaat aaagtctgtc | 3420 |
| atgccaaaag taaaaaaaaa aaaaaaaaaa aaaaaaaaaa aaaaaaaaaa aaaaaaaaaa | 3480 |
| aaaaaaaaaa a | 3491 |

<210> SEQ ID NO 2
<211> LENGTH: 606
<212> TYPE: DNA
<213> ORGANISM: Homo sapiens

<400> SEQUENCE: 2

| | |
|---|---|
| atgcggcgcg cgtggatcct gctcaccttg ggcttggtgg cctgcgtgtc ggcggagtcg | 60 |
| agagcagagc tgacatctga taaagacatg taccttgaca acagctccat tgaagaagct | 120 |
| tcaggagtgt atcctattga tgacgatgac tacgcttctg cgtctggctc gggagctgat | 180 |
| gaggatgtag agagtccaga gctgacaaca tctcgaccac ttccaaagat actgttgact | 240 |
| agtgctgctc caaaagtgga aaccacgacg ctgaatatac agaacaagat acctgctcag | 300 |
| acaaagtcac ctgaagaaac tgataaagag aaagttcacc tctctgactc agaaaggaaa | 360 |
| atggacccag ccgaagagga tacaaatgtg tatactgaga acactcaga cagtctgttt | 420 |
| aaacggacag aagtcctagc agctgtcatt gctggtggag ttattggctt tctctttgca | 480 |
| attttttctta tcctgctgtt ggtgtatcgc atgagaaaga aggatgaagg aagctatgac | 540 |
| cttggagaac gcaaaccatc cagtgctgct tatcagaagg cacctactaa ggagttttat | 600 |
| gcgtaa | 606 |

<210> SEQ ID NO 3
<211> LENGTH: 201
<212> TYPE: PRT
<213> ORGANISM: Homo sapiens

<400> SEQUENCE: 3

Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu Thr Thr Thr Leu Asn Ile Gln Asn Lys
                85                  90                  95

Ile Pro Ala Gln Thr Lys Ser Pro Glu Glu Thr Asp Lys Glu Lys Val
            100                 105                 110

```
His Leu Ser Asp Ser Glu Arg Lys Met Asp Pro Ala Glu Glu Asp Thr
        115                 120                 125

Asn Val Tyr Thr Glu Lys His Ser Asp Ser Leu Phe Lys Arg Thr Glu
130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr Arg Met Arg Lys Lys Asp Glu
            165                 170                 175

Gly Ser Tyr Asp Leu Gly Glu Arg Lys Pro Ser Ser Ala Ala Tyr Gln
            180                 185                 190

Lys Ala Pro Thr Lys Glu Phe Tyr Ala
            195                 200

<210> SEQ ID NO 4
<211> LENGTH: 183
<212> TYPE: PRT
<213> ORGANISM: Homo sapiens

<400> SEQUENCE: 4

Glu Ser Arg Ala Glu Leu Thr Ser Asp Lys Asp Met Tyr Leu Asp Asn
1               5                   10                  15

Ser Ser Ile Glu Glu Ala Ser Gly Val Tyr Pro Ile Asp Asp Asp Asp
                20                  25                  30

Tyr Ala Ser Ala Ser Gly Ser Gly Ala Asp Glu Asp Val Glu Ser Pro
            35                  40                  45

Glu Leu Thr Thr Ser Arg Pro Leu Pro Lys Ile Leu Leu Thr Ser Ala
        50                  55                  60

Ala Pro Lys Val Glu Thr Thr Thr Leu Asn Ile Gln Asn Lys Ile Pro
65                  70                  75                  80

Ala Gln Thr Lys Ser Pro Glu Glu Thr Asp Lys Glu Lys Val His Leu
                85                  90                  95

Ser Asp Ser Glu Arg Lys Met Asp Pro Ala Glu Glu Asp Thr Asn Val
            100                 105                 110

Tyr Thr Glu Lys His Ser Asp Ser Leu Phe Lys Arg Thr Glu Val Leu
        115                 120                 125

Ala Ala Val Ile Ala Gly Gly Val Ile Gly Phe Leu Phe Ala Ile Phe
    130                 135                 140

Leu Ile Leu Leu Leu Val Tyr Arg Met Arg Lys Lys Asp Glu Gly Ser
145                 150                 155                 160

Tyr Asp Leu Gly Glu Arg Lys Pro Ser Ser Ala Ala Tyr Gln Lys Ala
                165                 170                 175

Pro Thr Lys Glu Phe Tyr Ala
            180
```